US012806395B2

(12) United States Patent
Lanigan

(10) Patent No.: US 12,806,395 B2
(45) Date of Patent: Nov. 24, 2026

(54) INJECTION ASSEMBLY APPARATUSES, SYSTEMS, AND METHODS

(71) Applicant: DEKA Products Limited Partnership, Manchester, NH (US)

(72) Inventor: Richard J. Lanigan, Concord, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 1002 days.

(21) Appl. No.: 17/896,402

(22) Filed: Aug. 26, 2022

(65) Prior Publication Data

US 2023/0060176 A1 Mar. 2, 2023

Related U.S. Application Data

(60) Provisional application No. 63/237,266, filed on Aug. 26, 2021.

(51) Int. Cl.

| | |
|---|---|
| ***A61M 39/02*** | (2006.01) |
| ***A61J 1/05*** | (2006.01) |
| *A61J 1/20* | (2006.01) |

(52) U.S. Cl.

CPC ................ *A61M 39/02* (2013.01); *A61J 1/05* (2013.01); *A61J 1/2006* (2015.05)

(58) Field of Classification Search

CPC .............. A61M 39/02; A61M 39/0247; A61M 2039/0202; A61M 2039/0205;

(Continued)

(56) References Cited

U.S. PATENT DOCUMENTS

| | | | |
|---|---|---|---|
| 1,934,046 | A | 11/1933 | Demarchi |
| 2,512,568 | A | 6/1950 | Saffir |

(Continued)

FOREIGN PATENT DOCUMENTS

| | | |
|---|---|---|
| CA | 225208 | 10/2023 |
| CA | 219028 | 1/2025 |

(Continued)

OTHER PUBLICATIONS

"Cleo 90 Infusion Set Training Guide" [online] Smiths Medical MD, Inc. pp. 1, https://manualzz.com/doc/6784816/to-the-cleo-training-guide (Retrieved Sep. 1, 2021).

(Continued)

*Primary Examiner* — Kami A Bosworth
*Assistant Examiner* — Antarius S Daniel
(74) *Attorney, Agent, or Firm* — Toohey Law Group, LLC; Kevin D. Mandro

(57) ABSTRACT

An injection port assembly may comprise a support body having a receptacle associated with a passage through the support body. The receptacle may have at least one recess in an end surface of the receptacle. The receptacle may have a plurality of retainer members. The assembly may further comprise a peripheral rim rib about a periphery of the support body and a number of additional ribs extending from the receptacle to the peripheral rim rib. The assembly may further comprise a delivery assembly coupled within the receptacle via the retainer members. The delivery assembly may have a cannula extending through the passage. The delivery assembly may have an injection receiving volume within the delivery assembly in fluid communication with a lumen of the cannula but otherwise fluidically sealed by a self-sealing barrier. There may be a sole externally accessible portion of the barrier aligned with an axis of the lumen.

25 Claims, 12 Drawing Sheets

(58) Field of Classification Search
CPC .. A61M 2039/0258; A61M 2039/0232; A61M 5/158; A61M 5/14244; A61M 5/14288; A61M 5/14248; A61M 2005/1585; A61M 2005/1586; A61M 2005/1587; A61M 2005/14252; A61M 2005/14284; A61F 2013/00327
See application file for complete search history.

(56) References Cited

U.S. PATENT DOCUMENTS

| | | | |
|---|---|---|---|
| 2,743,723 | A | 5/1956 | Hein |
| 2,945,496 | A | 7/1960 | Fosdal |
| 3,122,138 | A | 2/1964 | Geary |
| 3,856,009 | A | 12/1974 | Winnie |
| 4,284,077 | A | 8/1981 | Wagner |
| 4,299,219 | A | 11/1981 | Norris, Jr. |
| D265,590 | S | 7/1982 | Gauvry |
| 4,723,940 | A | 2/1988 | Wiegerinck |
| 4,755,173 | A | 7/1988 | Konopka et al. |
| 4,838,863 | A | 6/1989 | Allard et al. |
| 5,176,662 | A | 1/1993 | Bartholomew et al. |
| 5,257,980 | A | 11/1993 | Van Antwerp et al. |
| 5,320,607 | A | 6/1994 | Ishibashi |
| 5,395,379 | A | 3/1995 | Deutchman |
| D363,542 | S | 10/1995 | Parris et al. |
| 5,478,315 | A | 12/1995 | Brothers et al. |
| 5,522,803 | A | 6/1996 | Teissen-Simony |
| 5,584,813 | A | 12/1996 | Livingston et al. |
| 5,743,891 | A | 4/1998 | Tolkoff et al. |
| D395,501 | S | 6/1998 | Erskine et al. |
| 5,782,871 | A | 7/1998 | Fujiwara et al. |
| D403,398 | S | 12/1998 | Guala et al. |
| 5,851,197 | A | 12/1998 | Marano et al. |
| D405,882 | S | 2/1999 | Yale |
| 5,879,311 | A | 3/1999 | Duchon et al. |
| 5,968,011 | A | 10/1999 | Larsen et al. |
| D416,086 | S | 11/1999 | Parris et al. |
| 5,980,506 | A | 11/1999 | Mathiasen |
| D417,733 | S | 12/1999 | Howell et al. |
| 6,017,328 | A | 1/2000 | Fischell et al. |
| 6,056,718 | A | 5/2000 | Funderburk et al. |
| 6,086,545 | A | 7/2000 | Roe et al. |
| 6,086,575 | A | 7/2000 | Mejslov |
| 6,093,172 | A | 7/2000 | Funderburk et al. |
| 6,123,690 | A | 9/2000 | Mejslov |
| 6,183,446 | B1 | 2/2001 | Jeanbourquin |
| 6,254,580 | B1 | 7/2001 | Svedman |
| 6,261,272 | B1 | 7/2001 | Gross et al. |
| 6,293,925 | B1 | 9/2001 | Safabash et al. |
| 6,302,866 | B1 | 10/2001 | Marggi |
| 6,355,021 | B1 | 3/2002 | Nielsen et al. |
| 6,379,339 | B1 | 4/2002 | Klitgaard et al. |
| 6,461,329 | B1 | 10/2002 | Van Antwerp et al. |
| D465,845 | S | 11/2002 | Swenson |
| D465,846 | S | 11/2002 | Hwang |
| 6,482,176 | B1 | 11/2002 | Wich |
| D472,630 | S | 4/2003 | Douglas et al. |
| 6,558,402 | B1 | 5/2003 | Chelak et al. |
| D476,418 | S | 6/2003 | Sprieck et al. |
| 6,579,267 | B2 | 6/2003 | Lynch et al. |
| 6,582,403 | B1 | 6/2003 | Bierman et al. |
| 6,589,229 | B1 | 7/2003 | Connelly et al. |
| 6,605,058 | B1 | 8/2003 | Wich |
| 6,607,509 | B2 | 8/2003 | Bobroff et al. |
| D484,242 | S | 12/2003 | Wilkinson |
| D484,976 | S | 1/2004 | Wilkinson |
| 6,685,674 | B2 | 2/2004 | Douglas et al. |
| 6,699,218 | B2 | 3/2004 | Flaherty et al. |
| D488,230 | S | 4/2004 | Ignotz et al. |
| 6,736,797 | B1 | 5/2004 | Larsen et al. |
| 6,749,589 | B1 | 6/2004 | Douglas et al. |
| 6,830,562 | B2 | 12/2004 | Mogensen et al. |
| 6,835,190 | B2 | 12/2004 | Nguyen |
| 6,887,417 | B1 | 5/2005 | Gawreluk et al. |
| D507,833 | S | 7/2005 | Coss |
| 6,923,791 | B2 | 8/2005 | Douglas |
| 6,926,694 | B2 | 8/2005 | Marano-Ford et al. |
| 6,949,084 | B2 | 9/2005 | Marggi et al. |
| 6,994,691 | B2 | 2/2006 | Ejlersen |
| 7,056,302 | B2 | 6/2006 | Douglas |
| 7,060,054 | B2 | 6/2006 | Nissels |
| 7,066,885 | B2 | 6/2006 | Erickson et al. |
| 7,066,922 | B2 | 6/2006 | Angel et al. |
| 7,070,580 | B2 | 7/2006 | Nielsen |
| 7,083,597 | B2 | 8/2006 | Lynch et al. |
| 7,115,111 | B2 | 10/2006 | Haindl |
| 7,147,623 | B2 | 12/2006 | Mathiasen |
| 7,147,624 | B2 | 12/2006 | Hirsiger et al. |
| 7,214,207 | B2 | 5/2007 | Lynch et al. |
| D547,859 | S | 7/2007 | Choi |
| 7,258,678 | B2 | 8/2007 | Wilkinson |
| D554,253 | S | 10/2007 | Kornerup |
| 7,303,543 | B1 | 12/2007 | Maule et al. |
| 7,303,544 | B2 | 12/2007 | Bütikofer et al. |
| 7,309,326 | B2 | 12/2007 | Fangrow, Jr. |
| 7,338,465 | B2 | 3/2008 | Patton |
| 7,377,908 | B2 | 5/2008 | Buetikofer et al. |
| 7,407,493 | B2 | 8/2008 | Cane' |
| D576,267 | S | 9/2008 | Mogensen et al. |
| 7,431,876 | B2 | 10/2008 | Mejlhede et al. |
| 7,455,663 | B2 | 11/2008 | Bikovsky |
| 7,481,794 | B2 | 1/2009 | Jensen |
| 7,494,481 | B2 | 2/2009 | Moberg et al. |
| 7,510,543 | B2 | 3/2009 | Michels et al. |
| 7,513,887 | B2 | 4/2009 | Halseth et al. |
| 7,520,867 | B2 | 4/2009 | Bowman et al. |
| 7,524,309 | B2 | 4/2009 | McConnell et al. |
| D592,310 | S | 5/2009 | Leatt |
| 7,549,976 | B2 | 6/2009 | Michels et al. |
| 7,569,034 | B2 | 8/2009 | Lynch et al. |
| 7,578,807 | B2 | 8/2009 | Wyss et al. |
| D600,341 | S | 9/2009 | Loerwald |
| 7,585,287 | B2 | 9/2009 | Bresina et al. |
| 7,594,902 | B2 | 9/2009 | Horisberger et al. |
| D604,836 | S | 11/2009 | Crawford et al. |
| D604,837 | S | 11/2009 | Crawford et al. |
| D604,838 | S | 11/2009 | Crawford et al. |
| D604,839 | S | 11/2009 | Crawford et al. |
| 7,621,395 | B2 | 11/2009 | Mogensen et al. |
| D605,287 | S | 12/2009 | Crawford et al. |
| D605,300 | S | 12/2009 | Mazzarolo |
| 7,648,494 | B2 | 1/2010 | Kornerup et al. |
| D609,804 | S | 2/2010 | Uchida et al. |
| D609,806 | S | 2/2010 | Uchida et al. |
| 7,666,150 | B2 | 2/2010 | Douglas et al. |
| 7,678,079 | B2 | 3/2010 | Shermer et al. |
| 7,682,338 | B2 | 3/2010 | Griffin |
| 7,699,807 | B2 | 4/2010 | Faust et al. |
| 7,699,808 | B2 | 4/2010 | Marrs et al. |
| 7,704,229 | B2 | 4/2010 | Moberg et al. |
| D616,094 | S | 5/2010 | Boone, III et al. |
| 7,731,691 | B2 | 6/2010 | Cote et al. |
| 7,736,338 | B2 | 6/2010 | Kavazov et al. |
| 7,740,600 | B2 | 6/2010 | Slatkine et al. |
| 7,758,516 | B2 | 7/2010 | Perez |
| 7,766,867 | B2 | 8/2010 | Lynch et al. |
| 7,766,874 | B2 | 8/2010 | Liniger |
| 7,771,393 | B2 | 8/2010 | Liniger et al. |
| 7,789,857 | B2 | 9/2010 | Moberg et al. |
| 7,815,607 | B2 | 10/2010 | Rutti et al. |
| D627,459 | S | 11/2010 | Uchida et al. |
| 7,841,991 | B2 | 11/2010 | Douglas et al. |
| 7,850,652 | B2 | 12/2010 | Liniger et al. |
| 7,850,658 | B2 | 12/2010 | Faust et al. |
| 7,867,199 | B2 | 1/2011 | Mogensen et al. |
| 7,867,200 | B2 | 1/2011 | Mogensen et al. |
| 7,879,010 | B2 | 2/2011 | Hunn et al. |
| 7,887,737 | B2 | 2/2011 | Mejlhede et al. |
| 7,892,216 | B2 | 2/2011 | Fangrow, Jr. |
| 7,896,844 | B2 | 3/2011 | Thalmann et al. |
| 7,901,382 | B2 | 3/2011 | Daily et al. |
| 7,909,791 | B2 | 3/2011 | Liniger et al. |
| 7,931,615 | B2 | 4/2011 | Fangrow, Jr. |
| 7,935,104 | B2 | 5/2011 | Yodfat et al. |

(56) References Cited

U.S. PATENT DOCUMENTS

| | | | |
|---|---|---|---|
| 7,946,984 | B2 | 5/2011 | Brister et al. |
| 7,951,080 | B2 | 5/2011 | Taub |
| 7,951,122 | B2 | 5/2011 | Shekalim |
| 7,955,297 | B2 | 6/2011 | Radmer et al. |
| 7,981,085 | B2 | 7/2011 | Ethelfeld |
| 7,985,199 | B2 | 7/2011 | Kornerup et al. |
| 7,985,203 | B2 | 7/2011 | Haueter et al. |
| 7,993,306 | B2 | 8/2011 | Marrs et al. |
| 8,002,752 | B2 | 8/2011 | Yodfat et al. |
| 8,012,126 | B2 | 9/2011 | Tipsmark et al. |
| 8,025,658 | B2 | 9/2011 | Chong et al. |
| 8,043,262 | B2 | 10/2011 | Streit et al. |
| 8,043,317 | B2 | 10/2011 | Fritz et al. |
| 8,062,250 | B2 | 11/2011 | Mogensen et al. |
| 8,062,253 | B2 | 11/2011 | Nielsen et al. |
| 8,152,771 | B2 | 4/2012 | Mogensen et al. |
| 8,157,773 | B2 | 4/2012 | Tashjian |
| 8,162,892 | B2 | 4/2012 | Mogensen et al. |
| 8,167,841 | B2 | 5/2012 | Teisen-Simony et al. |
| 8,172,803 | B2 | 5/2012 | Morrissey et al. |
| 8,172,805 | B2 | 5/2012 | Mogensen et al. |
| 8,221,355 | B2 | 7/2012 | Kornerup et al. |
| 8,226,614 | B2 | 7/2012 | Turner et al. |
| 8,246,588 | B2 | 8/2012 | Gyrn |
| 8,262,618 | B2 | 9/2012 | Scheurer |
| 8,287,516 | B2 | 10/2012 | Kornerup et al. |
| 8,292,849 | B2 | 10/2012 | Bobroff et al. |
| 8,298,172 | B2 | 10/2012 | Nielsen et al. |
| 8,303,545 | B2 | 11/2012 | Schraga |
| 8,303,549 | B2 | 11/2012 | Mejlhede et al. |
| 8,317,759 | B2 | 11/2012 | Moberg et al. |
| 8,323,250 | B2 | 12/2012 | Chong et al. |
| 8,343,115 | B2 | 1/2013 | Lynch et al. |
| 8,409,145 | B2 | 4/2013 | Raymond et al. |
| 8,430,850 | B2 | 4/2013 | Gyrn et al. |
| 8,435,211 | B2 | 5/2013 | Yodfat et al. |
| 8,439,838 | B2 | 5/2013 | Mogensen et al. |
| 8,449,479 | B2 | 5/2013 | Radzuinas et al. |
| D685,496 | S | 7/2013 | Lee |
| 8,475,410 | B2 | 7/2013 | Kaufmann et al. |
| 8,486,003 | B2 | 7/2013 | Nielsen |
| 8,506,585 | B2 | 8/2013 | Kube |
| 8,529,515 | B2 | 9/2013 | Woehr et al. |
| 8,551,047 | B2 | 10/2013 | Burns et al. |
| 8,562,567 | B2 | 10/2013 | Gundberg |
| 8,571,624 | B2 | 10/2013 | Stafford |
| D693,114 | S | 11/2013 | Lemanski |
| 8,579,863 | B2 | 11/2013 | Scherr |
| 8,617,126 | B2 | 12/2013 | Gross et al. |
| 8,628,498 | B2 | 1/2014 | Safabash et al. |
| 8,641,674 | B2 | 2/2014 | Bobroff et al. |
| 8,679,132 | B2 | 3/2014 | Deck |
| 8,690,775 | B2 | 4/2014 | Brister et al. |
| 8,696,570 | B2 | 4/2014 | Yodfat et al. |
| 8,709,033 | B2 | 4/2014 | Kim et al. |
| 8,715,232 | B2 | 5/2014 | Yodfat et al. |
| 8,734,391 | B2 | 5/2014 | Yodfat et al. |
| 8,740,851 | B2 | 6/2014 | Ethelfeld |
| 8,747,363 | B2 | 6/2014 | Neilsen et al. |
| D709,186 | S | 7/2014 | Boaz et al. |
| 8,790,311 | B2 | 7/2014 | Gryn |
| 8,795,230 | B2 | 8/2014 | Schoonmaker et al. |
| 8,795,234 | B2 | 8/2014 | Kadamus et al. |
| 8,795,309 | B2 | 8/2014 | Lacy |
| D713,957 | S | 9/2014 | Woehr et al. |
| 8,858,498 | B2 | 10/2014 | West |
| 8,882,710 | B2 | 11/2014 | Chong et al. |
| 8,882,711 | B2 | 11/2014 | Saulenas et al. |
| D720,466 | S | 12/2014 | Edding |
| 8,900,190 | B2 | 12/2014 | Chong et al. |
| 8,920,381 | B2 | 12/2014 | Ejlersen |
| 8,945,050 | B2 | 2/2015 | Wei |
| 8,945,057 | B2 | 2/2015 | Gyrn et al. |
| 8,956,330 | B2 | 2/2015 | Fangrow, Jr. |
| 8,961,469 | B2 | 2/2015 | Sonderegger et al. |
| 9,011,388 | B2 | 4/2015 | Schwartz et al. |
| 9,101,389 | B2 | 8/2015 | Havel et al. |
| 9,119,913 | B2 | 9/2015 | Lanigan |
| 9,211,379 | B2 | 12/2015 | Mejlhede et al. |
| 9,215,992 | B2 | 12/2015 | Donnay et al. |
| 9,220,833 | B2 | 12/2015 | Robert et al. |
| 9,220,838 | B2 | 12/2015 | Soma et al. |
| D747,456 | S | 1/2016 | Sonderegger et al. |
| D747,459 | S | 1/2016 | Sonderegger et al. |
| D747,472 | S | 1/2016 | Bradley et al. |
| 9,227,013 | B2 | 1/2016 | Lacy |
| 9,238,123 | B2 | 1/2016 | Weadock et al. |
| 9,254,373 | B2 | 2/2016 | Hørdum |
| 9,265,881 | B2 | 2/2016 | Montalvo et al. |
| 9,278,173 | B2 | 3/2016 | Mejlhede et al. |
| 9,295,786 | B2 | 3/2016 | Gottlieb et al. |
| D754,842 | S | 4/2016 | Sonderegger et al. |
| D754,843 | S | 4/2016 | Sonderegger et al. |
| 9,308,354 | B2 | 4/2016 | Farrell et al. |
| D756,504 | S | 5/2016 | Sonderegger et al. |
| 9,327,098 | B2 | 5/2016 | Kelvered et al. |
| 9,339,603 | B2 | 5/2016 | Gray et al. |
| 9,375,529 | B2 | 6/2016 | Searle et al. |
| 9,375,537 | B2 | 6/2016 | Montalvo et al. |
| 9,427,180 | B2 | 8/2016 | DiCesare et al. |
| 9,433,757 | B2 | 9/2016 | Constantineau et al. |
| 9,440,051 | B2 | 9/2016 | Gyrn |
| 9,480,792 | B2 | 11/2016 | Constantineau et al. |
| 9,511,189 | B2 | 12/2016 | O'Connor et al. |
| 9,522,228 | B2 | 12/2016 | Teutsch et al. |
| 9,522,229 | B2 | 12/2016 | Sonderegger et al. |
| 9,545,477 | B2 | 1/2017 | Chong et al. |
| 9,566,384 | B2 | 2/2017 | Gyrn et al. |
| 9,597,461 | B2 | 3/2017 | Aasmul |
| 9,610,401 | B2 | 4/2017 | Antonio et al. |
| 9,649,053 | B2 | 5/2017 | DiCesare et al. |
| D790,691 | S | 6/2017 | Davis et al. |
| 9,675,750 | B2 | 6/2017 | Grant et al. |
| 9,675,785 | B2 | 6/2017 | Constantineau et al. |
| 9,724,127 | B2 | 8/2017 | Gyrn |
| 9,731,069 | B2 | 8/2017 | Benéet al. |
| 9,744,295 | B2 | 8/2017 | Wyss et al. |
| D801,522 | S | 10/2017 | Shalom |
| 9,782,538 | B2 | 10/2017 | Cole et al. |
| 9,789,250 | B2 | 10/2017 | Hwang |
| 9,795,777 | B2 | 10/2017 | Sonderegger et al. |
| 9,821,113 | B2 | 11/2017 | Cole et al. |
| 9,844,330 | B2 | 12/2017 | Wilkinson |
| 9,872,642 | B2 | 1/2018 | Deck |
| 9,878,110 | B2 | 1/2018 | Cole et al. |
| 9,901,675 | B2 | 2/2018 | Ella et al. |
| 9,901,681 | B2 | 2/2018 | Sweeney et al. |
| D812,223 | S | 3/2018 | Evans et al. |
| D815,279 | S | 4/2018 | Darras |
| 9,943,332 | B2 | 4/2018 | Chong et al. |
| 9,943,643 | B2 | 4/2018 | Constantineau et al. |
| D817,482 | S | 5/2018 | Howell et al. |
| 9,968,742 | B2 | 5/2018 | Van Antwerp et al. |
| 9,987,476 | B2 | 6/2018 | Montalvo et al. |
| 10,071,209 | B2 | 9/2018 | Solomon et al. |
| 10,076,356 | B2 | 9/2018 | Hadvary et al. |
| 10,076,606 | B2 | 9/2018 | Ambruzs et al. |
| 10,080,582 | B2 | 9/2018 | Hadvary et al. |
| 10,080,839 | B2 | 9/2018 | Cole et al. |
| 10,105,484 | B2 | 10/2018 | Sonderegger et al. |
| 10,117,989 | B2 | 11/2018 | Hadvary et al. |
| 10,130,761 | B2 | 11/2018 | Searle et al. |
| D836,769 | S | 12/2018 | Kabel-Eckes |
| D839,423 | S | 1/2019 | Großer et al. |
| 10,194,938 | B2 | 2/2019 | Byager |
| 10,195,342 | B2 | 2/2019 | Cole et al. |
| D842,464 | S | 3/2019 | Davis et al. |
| 10,220,137 | B2 | 3/2019 | Sonderegger |
| 10,279,108 | B2 | 5/2019 | Teoh et al. |
| 10,369,277 | B2 | 8/2019 | Mogensen et al. |
| 10,413,661 | B2 | 9/2019 | Kamen et al. |
| D863,546 | S | 10/2019 | Converse |
| D883,474 | S | 5/2020 | Tipsmark |
| D884,160 | S | 5/2020 | Adams |

(56) References Cited

U.S. PATENT DOCUMENTS

| | | | | |
|---|---|---|---|---|
| 10,646,643 | B2 | 5/2020 | Cabiri et al. | |
| 10,682,462 | B2 | 6/2020 | Howell et al. | |
| D893,707 | S | 8/2020 | Burkholz et al. | |
| D900,308 | S | 10/2020 | Burkholz et al. | |
| 10,792,419 | B2 | 10/2020 | Kamen et al. | |
| D913,487 | S | 3/2021 | Orofino | |
| 10,933,191 | B2 | 3/2021 | Lawrence et al. | |
| D961,782 | S | 8/2022 | Locke et al. | |
| 11,458,292 | B2 | 10/2022 | Erichsen | |
| D973,202 | S | 12/2022 | Schuepbach | |
| D975,845 | S | 1/2023 | Kobayashi et al. | |
| 11,617,827 | B2 | 4/2023 | Mogensen et al. | |
| D995,103 | S | 8/2023 | Smith | |
| 11,786,653 | B2 * | 10/2023 | Gyrn | A61M 5/158 604/157 |
| D1,008,452 | S | 12/2023 | Lanigan | |
| D1,013,864 | S | 2/2024 | Lanigan | |
| D1,043,975 | S | 9/2024 | Cox et al. | |
| D1,043,976 | S | 9/2024 | Cannan et al. | |
| D1,057,941 | S | 1/2025 | Cannan et al. | |
| D1,064,312 | S | 2/2025 | Chae | |
| D1,077,238 | S | 5/2025 | Filgate et al. | |
| D1,090,862 | S | 8/2025 | Furtado et al. | |
| 2002/0055711 | A1 | 5/2002 | Lavi et al. | |
| 2002/0072720 | A1 | 6/2002 | Hague et al. | |
| 2002/0173769 | A1 | 11/2002 | Gray et al. | |
| 2004/0116866 | A1 | 6/2004 | Gorman et al. | |
| 2004/0158207 | A1 | 8/2004 | Hunn et al. | |
| 2005/0101932 | A1 | 5/2005 | Cote et al. | |
| 2005/0107743 | A1 | 5/2005 | Fangrow, Jr. | |
| 2005/0113761 | A1 | 5/2005 | Faust et al. | |
| 2005/0245956 | A1 | 11/2005 | Steinemann et al. | |
| 2005/0256460 | A1 | 11/2005 | Rome et al. | |
| 2005/0273076 | A1 | 12/2005 | Beasley et al. | |
| 2006/0184104 | A1 | 8/2006 | Cheney, II et al. | |
| 2006/0247574 | A1 | 11/2006 | Maule et al. | |
| 2007/0088254 | A1 | 4/2007 | DeStefano | |
| 2007/0191772 | A1 | 8/2007 | Wojcik | |
| 2007/0191773 | A1 | 8/2007 | Wojcik | |
| 2008/0154205 | A1 | 6/2008 | Wojcik | |
| 2008/0208139 | A1 | 8/2008 | Scheurer et al. | |
| 2008/0215003 | A1 * | 9/2008 | Kornerup | A61M 5/158 604/116 |
| 2008/0215006 | A1 | 9/2008 | Thorkild | |
| 2008/0249471 | A1 | 10/2008 | DeStefano et al. | |
| 2009/0012472 | A1 | 1/2009 | Ahm et al. | |
| 2009/0012473 | A1 | 1/2009 | Stettler et al. | |
| 2009/0069750 | A1 * | 3/2009 | Schraga | A61M 5/14248 604/539 |
| 2009/0076451 | A1 | 3/2009 | Teisen-Simony et al. | |
| 2009/0143763 | A1 | 6/2009 | Wyss et al. | |
| 2009/0198190 | A1 | 8/2009 | Jensen et al. | |
| 2009/0204077 | A1 | 8/2009 | Hasted et al. | |
| 2009/0216215 | A1 | 8/2009 | Thalmann et al. | |
| 2009/0218243 | A1 | 9/2009 | Gyrn et al. | |
| 2009/0326472 | A1 | 12/2009 | Carter et al. | |
| 2010/0004597 | A1 | 1/2010 | Gyrn et al. | |
| 2010/0036323 | A1 | 2/2010 | Smith | |
| 2010/0137695 | A1 * | 6/2010 | Yodfat | A61B 5/6849 604/272 |
| 2010/0160851 | A1 | 6/2010 | Dimalanta et al. | |
| 2010/0198157 | A1 | 8/2010 | Gyrn et al. | |
| 2010/0274200 | A1 | 10/2010 | Nielsen | |
| 2011/0009703 | A1 | 1/2011 | Smith | |
| 2011/0034883 | A1 | 2/2011 | Gyrn et al. | |
| 2011/0040263 | A1 | 2/2011 | Hørdum et al. | |
| 2011/0087159 | A1 | 4/2011 | Parihar et al. | |
| 2011/0098652 | A1 | 4/2011 | Hasted et al. | |
| 2011/0137257 | A1 | 6/2011 | Gyrn et al. | |
| 2012/0022461 | A1 | 1/2012 | Schubert et al. | |
| 2012/0046533 | A1 | 2/2012 | Voskanyan et al. | |
| 2012/0095406 | A1 * | 4/2012 | Gyrn | A61M 5/158 604/164.08 |
| 2012/0143135 | A1 | 6/2012 | Cole | |
| 2012/0150123 | A1 | 6/2012 | Lawrence et al. | |
| 2012/0265166 | A1 | 10/2012 | Yodfat | |
| 2012/0283646 | A1 | 11/2012 | Kouyoumijian | |
| 2013/0066293 | A1 | 3/2013 | Garfield et al. | |
| 2013/0197439 | A1 | 8/2013 | Melvin et al. | |
| 2013/0338594 | A1 | 12/2013 | Da Ros et al. | |
| 2014/0039453 | A1 | 2/2014 | Sonderegger | |
| 2014/0058353 | A1 | 2/2014 | Politis et al. | |
| 2014/0058360 | A1 | 2/2014 | Schoonmaker et al. | |
| 2014/0074028 | A1 * | 3/2014 | Sonderegger | A61M 25/0606 604/533 |
| 2014/0094756 | A1 | 4/2014 | Bobroff et al. | |
| 2014/0155679 | A1 | 6/2014 | Pesach et al. | |
| 2014/0155819 | A1 | 6/2014 | Amirouche et al. | |
| 2014/0275773 | A1 | 9/2014 | Tarazona et al. | |
| 2014/0276557 | A1 | 9/2014 | Vaishya | |
| 2014/0296782 | A1 | 10/2014 | Ulrich et al. | |
| 2015/0025478 | A1 | 1/2015 | Hibdon et al. | |
| 2015/0051583 | A1 | 2/2015 | Horvath et al. | |
| 2015/0112302 | A1 | 4/2015 | Chattaraj et al. | |
| 2015/0164545 | A1 | 6/2015 | Gyrn | |
| 2015/0238705 | A1 | 8/2015 | Gravesen et al. | |
| 2016/0015303 | A1 | 1/2016 | Bernstein et al. | |
| 2016/0129203 | A1 | 5/2016 | Chong et al. | |
| 2016/0339186 | A1 | 11/2016 | Hagy et al. | |
| 2017/0281863 | A1 * | 10/2017 | Kamen | A61M 5/162 |
| 2017/0303831 | A1 | 10/2017 | Tsubouchi et al. | |
| 2018/0200412 | A1 | 7/2018 | Dang et al. | |
| 2019/0009019 | A1 | 1/2019 | Shor et al. | |
| 2019/0060562 | A1 * | 2/2019 | Olivas | A61M 5/14248 |
| 2019/0151561 | A1 | 5/2019 | Bernhard et al. | |
| 2019/0216397 | A1 | 7/2019 | Yavorsky et al. | |
| 2019/0336078 | A1 | 11/2019 | Dang et al. | |
| 2020/0164159 | A1 | 5/2020 | Chattaraj et al. | |
| 2020/0289748 | A1 | 9/2020 | Lanigan et al. | |
| 2020/0368515 | A1 | 11/2020 | Erichsen | |
| 2021/0268179 | A1 | 9/2021 | Schøndorff et al. | |
| 2021/0386930 | A1 | 12/2021 | Lanigan et al. | |
| 2022/0117627 | A1 | 4/2022 | Garai | |
| 2022/0125346 | A1 | 4/2022 | Stafford | |
| 2022/0202366 | A1 | 6/2022 | Mitchell et al. | |
| 2022/0379019 | A1 | 12/2022 | Lanigan et al. | |
| 2023/0060176 | A1 | 3/2023 | Lanigan | |
| 2023/0062738 | A1 | 3/2023 | Lanigan et al. | |
| 2024/0066217 | A1 | 2/2024 | Lanigan et al. | |
| 2024/0216605 | A1 | 7/2024 | Lanigan | |
| 2024/0216606 | A1 | 7/2024 | Lanigan | |
| 2024/0261498 | A1 | 8/2024 | Lanigan | |
| 2024/0261499 | A1 | 8/2024 | Lanigan | |
| 2024/0293615 | A1 | 9/2024 | Lanigan | |
| 2024/0382674 | A1 | 11/2024 | Lanigan | |
| 2025/0082271 | A1 | 3/2025 | Oakes | |
| 2025/0107939 | A1 | 4/2025 | Gardner et al. | |

FOREIGN PATENT DOCUMENTS

| | | | |
|---|---|---|---|
| CN | 203494005 | U | 3/2014 |
| CN | 203609736 | U | 5/2014 |
| CN | 203815967 | U | 9/2014 |
| CN | 104302333 | A | 1/2015 |
| CN | 109069734 | A | 12/2018 |
| CN | 202230824756.3 | | 9/2023 |
| CN | 202330222706.2 | | 11/2023 |
| DE | 3708031 | A1 | 11/1987 |
| DE | 29905072 | U1 | 9/1999 |
| EP | 1539281 | B1 | 5/2007 |
| EP | 1691877 | B1 | 12/2013 |
| EP | 2712642 | A1 | 4/2014 |
| EP | 2713879 | B1 | 7/2017 |
| JP | 2014510574 | A | 5/2014 |
| JP | D2021-01054 | | 7/2022 |
| WO | WO2004020035 | A1 | 3/2004 |
| WO | WO2012/134588 | A1 | 10/2012 |

(56) References Cited

FOREIGN PATENT DOCUMENTS

| | | | |
|---|---|---|---|
| WO | WO2013/070715 | A1 | 5/2013 |
| WO | WO2015095342 | A1 | 6/2015 |

OTHER PUBLICATIONS

Heinemann, Lutz and Lars Krinelke "Insulin Infusion Set: The Achilles Heel of Continuous Subcutaneous Insulin Infusion" [online] Journal of Diabetes Science and Technology vol. 6, No. 4, Jul. 2012. pp. 954-964 doi: 10.1177/193229681200600429.
"Spring Universal Infusion Set Quick Guide" [online] Spring-set Health Solutions Ltd. pp. 1-2, https://www.slideshare.net/springnowl/spring-universal-guide?from_action=save (Retrieved Sep. 8, 2021).
International Search Report and Written Opinion date of mailing Jul. 31, 2020 received in International patent application PCT/US2020/019287 from the European Patent Office as International Searching Authority, European Patent Office, P.B. 5818 Patentlaan 2 NL—2280 HV Rijswijk (pp. 1-16).
International Search Report and Written Opinion date of mailing Jan. 13, 2023 received in International patent application PCT/US2022/041649 from the European Patent Office as International Searching Authority, European Patent Office, P.B. 5818 Patentlaan 2 NL—2280 HV Rijswijk (pp. 1-26).
International Search Report and Written Opinion date of mailing Nov. 23, 2022 received in International patent application PCT/US2022/041652 from the European Patent Office as International Searching Authority, European Patent Office, P.B. 5818 Patentlaan 2 NL—2280 HV Rijswijk (pp. 1-16).
U.S. Appl. No. 17/896,395, filed Aug. 26, 2022.
U.S. Appl. No. 29/805,354, filed Aug. 26, 2021.
U.S. Appl. No. 29/851,249, filed Aug. 26, 2022.
DE3708031A1, Unverified machine translation from Espacenet.
DE29905072U1, Unverified machine translation from Espacenet.
CN203494005U, Unverified machine translation from Espacenet.
CN109069734A, Unverified machine translation from Espacenet.
CN104302333A, Unverified machine translation from Espacenet.
CN203815967U, Unverified machine translation from Espacenet.
CN203609736U, Unverified machine translation from Espacenet.
PharmaSens seeks FDA Approval for new insulin pump. Online, published date Jan. 2, 2024. Retrieved on May 8, 2024 from URL:https://www.medicaldevice-network.com/news/pharmasens-fda-approval-insulin-pump/.
MIT jet-injector provides a needle-free alternative to medicine delivery. Online, published date May 24, 2012. Retrieved on May 8, 2024 from URL: https://newatlas.com/jet-injection-system-mit/22673/.
MiniMed Mio Advance Infusion Set, announced in YouTube on May 7, 2019 [Online]. [Retrieved on Aug. 2, 2023], Available from the internet URL:https://www.youtube.com/watch?v=2For6SAvxRQ (Year: 2022).
Neria Guard Infusion Set, announced in You Tube on May 17, 2022 [Online]. [Retrieved on Aug. 2, 2023], Available from the internet URL:https://www.youtube.com/watch?v=VUoLi-_gcyE (Year: 2023).
Autosoft XC Infusion Set. Product Support Page[Online]. Tandemdiabetes.com 2023. [Retrieved on Aug. 2, 2023]. Retrieved from the Internet: URL:https://support.tandemdiabetes.com/hc/en-us/articles/360039015054/ (Year: 2023).
Tapecon. using Adhesive Constructions to Improve Chain of Custody Sleep Apnea Tests. No Publication Date. Retrieved Feb. 19, 2025. https://www.tapecon.com/blog/adhesive-constructions-chain-of-custody-sleep-apnea-tests.
Medical Design & Outsourcing. new 3M Durapore Advanced Surgical Tape Offers Adhesive Innovation. Oct. 25, 2018. https://www.medicaldesignandoutsourcing.com/new-3m-durapore-advanced-surgical-tape-offers-adhesive-innovation/.
Tandem Varisoft Infusion Sets. 2024. Retrieived Nov. 16, 2024. https://doubekmedical.com/product/tandem-varisoft-infusion-sets/.
Tandem Autosoft 90 Infusion Sets. 2024. Retrieved Nov. 16, 2024. https://tinyurl.com/y38tt4fu.

* cited by examiner

INJECTION ASSEMBLY APPARATUSES, SYSTEMS, AND METHODS

CROSS-REFERENCE TO RELATED APPLICATIONS

This application claims the benefit of U.S. Provisional Application Ser. No. 63/237,266, filed Aug. 26, 2021 and entitled Injection Assembly Apparatuses, Systems, and Methods which is hereby incorporated by reference herein in its entirety.

BACKGROUND

This application relates generally to parenteral agent delivery, and more particularly, to multi-use infusion ports and methods for the use thereof.

DESCRIPTION OF RELATED ART

Many potentially valuable medicines or compounds, including biologicals, are not orally active due to poor absorption, hepatic metabolism or other pharmacokinetic factors. Additionally, some therapeutic compounds, although they can be orally administered, are sometimes required to be taken so often that it is difficult for a patient to maintain the desired schedule. In these cases, parenteral delivery is often employed or could be employed.

Effective parenteral delivery routes of drugs, other fluid, and compounds such as subcutaneous injection, intramuscular injection, and intravenous (IV) administration include puncture of the skin with a needle or stylet. Insulin is an example of a therapeutic fluid that is self-injected by millions of diabetic patients. In the case of insulin (as well as various other self-injected drugs), frequent injections may be necessary depending on the patient. In some cases of diabetes, several self-administered injections per day may be required to maintain a euglycemic state. Regardless of the disease or agent, such repetitive self-injection can adversely impact quality of life and may effect patient compliance with their prescribed delivery routine. As a result, patient outcomes may be negatively affected. Each time the agent is self-injected, a delivery sharp may puncture the skin with users being subjected to potential pain, discomfort, fear, stress, and anxiety. Additionally, scarring or bruising at injection sites may be common. Quality of life impacts may be heightened in certain patient populations such as children who may often have higher aversion to injections. Patients who require more than one parenteral agent to manage a condition or for patients with more than one condition for which self-injections of different agents are prescribed may likewise experience more pronounced impacts.

Users of parenterally delivered drugs may benefit from a device that would decrease the need for repeated puncture of the skin surface while still allowing a route of parenteral agent administration. There have been efforts to design portable and wearable devices for the controlled delivery of agents over a period of time. Such devices are known to have a reservoir such as a cartridge, syringe, or bag, and to be electronically controlled. These devices suffer from a number of drawbacks including the malfunction rate and the considerable expense associated with acquiring the devices and supplying them with consumables. Reducing the size, weight, and cost of these devices is also an ongoing challenge. Additionally, these devices often may be difficult to conceal and may require a run of tubing which can snag as a user participates in quotidian activities. Activities such as swimming or bathing may require the device to be removed. Some such devices may also have failure modes in which a user may not be alerted when agent delivery deviates from a prescribed or programmed rate.

SUMMARY

In accordance with an exemplary embodiment of the present disclosure an injection port assembly for delivery of multiple daily injections to a patient may comprise a support body. The support body may comprise a main body. The support body may further comprise a receptacle including a receptacle wall extending from a first face of the main body and surrounding a passage through the main body. The receptacle wall may include at least one notch recessed into a face of the receptacle wall most distal to the main body and a plurality of cantilevered retainer members. The support body may further comprise a plurality of sections proud of the first face. The sections may include a peripheral rim at the periphery of the main body and a number of proud sections extending from the receptacle wall to the peripheral rim. The injection port assembly may further comprise an adhering body attached to a second face of the main body opposite the first. The injection port assembly may further comprise a delivery assembly captured within the receptacle by the retainer members. The delivery assembly may have a cannula extending through the passage and a barrier element forming a fluid tight seal against an injection receiving volume defined in an enlarged end region of the cannula. The may be a sole externally accessible portion of the barrier element which may be aligned with an axis of the cannula.

In some embodiments, at least a portion of the receptacle wall most distal to the first face may include a taper. In some embodiments, the notches may include a taper at least at a portion of each notch which is most distal to the first face. In some embodiments, each of the retainer members may include a ramped latching protuberance at an unsupported end of each of the retainer members. In some embodiments, the delivery assembly may include a set of notches each configured to engage with a retainer member of the plurality of retainer members. In some embodiments, the delivery assembly may include a number of ear projections equal to the number of notches in the receptacle wall. Each ear projection may be disposed in one of the notches in the receptacle wall. In some embodiments, the barrier element may be constructed of a self-sealing material which self-seals after removal of a deliver sharp that has pierced the barrier element. In some embodiments, the injection port assembly may further comprise a delivery implement adapter. The adapter may be configured to couple to the support body. In some embodiments, the adapter may include an adapter receptacle for accepting a delivery implement. The adapter receptacle may be disposed over the sole externally accessible portion of the barrier element when coupled to the support body. In some embodiments, the receptacle wall may include a number of ledges and the adapter may include a number of latching arms. Each latch arm may be configured to engage with a ledge of the number of ledges. In some embodiments, the sole exposed portion of the barrier element may be spaced from the injection receiving volume by a barrier distance and the adapter may include a stop which limits a delivery sharp of a delivery implement from advancing into the injection port assembly to a depth greater than the barrier distance plus a partial percentage of a height of the injection receiving volume. In some embodiments, the barrier element may include a cavity into which the enlarged end region extends. An outwardly facing sealing surface of the enlarged region may form a fluid tight seal against the barrier. A portion of the cavity most distal the outlet of the cannula may be disposed adjacent open space within the injection receiving volume.

In accordance with another exemplary embodiment of the present disclosure an injection port assembly for delivery of multiple daily injections to a patient may comprise a support body. The injection port may further comprise a receptacle including a receptacle wall surrounding a passage through the support body. The receptacle wall may include at least one notch recessed into an end surface of the receptacle wall. The receptacle wall may include a plurality of cantilevered retainer members. The injection port may further comprise a plurality of ribs including a peripheral rim rib around the periphery of the support body and a number of additional ribs extending from the receptacle wall to the peripheral rim rib. The injection port assembly may further comprise an adhering body attached to the support body. The injection port assembly may further comprise a delivery assembly configured to couple within the receptacle by engagement with the retainer members. The delivery assembly may have a cannula extending through the passage and may include an enlarged end region which forms an injection receiving volume. The delivery assembly may have a barrier element in fluid tight relationship with a portion of the enlarged region and may have a sole externally accessible portion aligned with an axis of the cannula.

In some embodiments, the receptacle wall may include a tapered portion. In some embodiments, the notches may include a tapered portion. In some embodiments, each of the retainer members may include a ramped latching protuberance at an unsupported end of each of the retainer members. In some embodiments, the delivery assembly includes a set of retention recesses each configured to engage with a retainer member of the plurality of retainer members. In some embodiments, the delivery assembly may include a number of ear projections equal to the number of notches in the receptacle wall. Each ear projection may be disposed in one of the notches in the receptacle wall when the delivery assembly is coupled within the receptacle. In some embodiments, the barrier element may be constructed of a self-sealing elastomer. In some embodiments, the injection port assembly may further comprise a delivery implement adapter configured to couple to the receptacle wall. In some embodiments, the adapter may include an adapter receptacle for accepting a delivery implement, the adapter receptacle disposed over the sole externally accessible portion of the barrier element when coupled to the support body. In some embodiments, the receptacle wall may include a number of ledges and the adapter may include a number of latching arms. Each latch arm may be configured to engage with a ledge of the number of ledges. In some embodiments, the sole exposed portion of the barrier element may be spaced from the injection receiving volume by a barrier distance and the adapter may include a stop which limits a delivery sharp of a delivery implement from advancing into the injection port assembly to a depth greater than the barrier distance plus a partial percentage of a height of the injection receiving volume. In some embodiments, the enlarged end region may extend into a receptacle of the barrier element. The end region may have an outwardly facing sealing surface which forms a fluid tight seal against barrier element.

In accordance with another exemplary embodiment of the present disclosure an injection port assembly for delivery of multiple daily injections to a patient may comprise a support body having a receptacle associated with a passage through the support body. The receptacle may have at least one notched recess in an end surface of the receptacle. The receptacle may have a plurality of cantilevered retainer member. The injection port assembly may further comprise a plurality of ribs including a peripheral rim rib about a periphery of the support body and a number of additional ribs extending from the receptacle to the peripheral rim rib. The injection port assembly may further comprise a delivery assembly latched within the receptacle via the retainer members. The delivery assembly may have a cannula extending through the passage. The delivery assembly may have an injection receiving volume within the delivery assembly in fluid communication with a lumen of the cannula and otherwise sealed from the surrounding environment by a self-sealing barrier. There may be a sole externally accessible portion of the barrier which may be aligned with an axis of the lumen.

In accordance with another exemplary embodiment of the present disclosure a method of delivering a plurality of injections of over a period of time may comprise adhering a support body to a surface. The method may further comprise triggering an actuation assembly of an inserter to which the support body is coupled by withdrawing the inserter from the surface. The method may further comprise driving, with the actuation assembly, a sharp bearing body carrying a delivery assembly toward a receptacle of the support body and puncturing the surface with an insertion sharp of the sharp bearing body. The method may further comprise coupling the delivery assembly within the receptacle and retracting the sharp bearing body and insertion sharp, a cannula of the delivery assembly being left in a puncturing position which respect to the surface. The method may further comprise injecting agent into an injection receiving volume of the delivery assembly which is in fluid communication with the cannula. The method may further comprise injecting, at least one additional time, agent into the injection receiving volume.

In some embodiments, the method may further comprise puncturing a barrier element of the delivery assembly with a delivery sharp. In some embodiments, the method may further comprise attaching an adapter to the support body. In some embodiments, the method may further comprise advancing a delivery implement into the adapter. In some embodiments, the method may further comprise inhibiting displacement of the delivery implement such that a delivery sharp of the delivery implement is prevented from contacting the cannula of the delivery assembly. In some embodiments, the method may further comprise guiding a delivery sharp of a delivery implement into the injection receiving volume with the adapter. In some embodiments, the method may further comprise aligning a delivery sharp of a delivery implement via the adapter with a sole exposed surface of a barrier element separating the injection receiving volume from the surrounding environment. In some embodiments, coupling the delivery assembly within the receptacle may comprise engaging a set of latch projections of the receptacle with an engagement surface of the delivery assembly. In some embodiments, the method may further comprise piercing a barrier separating the injection receiving volume from the surrounding environment with a delivery sharp. In some embodiments, the method may further comprise separating a delivery implement from the delivery assembly and fluidically sealing the injection receiving volume from fluid transfer other than through the cannula.

In accordance with still another example embodiment of the present disclosure a medical agent delivery system may comprise a delivery set including a base and a cannula which extends from the base for delivery of agent into a patient. The system may further comprise a medication delivery pump including an agent reservoir. The system may further comprise a tubing connector and a run of tubing which extends from a point on the pump in fluid communication with the agent reservoir to the tubing connector. The tubing connector may include a first delivery projection in fluid communication with the tubing and at least one first connection interface configured to engage with the delivery set. The system may further comprise a second connector including a second delivery sharp and at least one second connection interface configured to engage with the delivery set. The second connector may include an injection receiving volume in fluid communication with the second delivery sharp and a septum separating the injection receiving volume from the surrounding environment.

In some embodiments, the pump may include a controller configured to govern operation of the pump to dispense agent according to a predetermine delivery prescription. In some embodiments, the septum may be constructed of a self-sealing material which forms a fluid tight seal after a sharp which has punctured the septum is removed. In some embodiments, the delivery set may include a fluid receiving volume in fluid communication with the cannula and otherwise sealed from the surrounding environment by a self-sealing barrier. In some embodiments, the first delivery projection may be in fluid communication with fluid receiving volume when the at least one first connection interface is engaged with the delivery set. In some embodiments, the second delivery projection may be in fluid communication with the fluid receiving volume when the at least one second connection interface is engaged with the delivery set. In some embodiments, the delivery set may include a delivery assembly which is coupled into a receptacle defined on the base. In some embodiments, each of the at least one first connection interface may be identical to a corresponding one of the at least one second connection interface. In some embodiments, the first and second delivery projections may be oriented parallel to the base when the tubing connector and second connector are respectively coupled to the base. In some embodiments, the first and second delivery projections may be oriented parallel to an axis of the cannula when the tubing connector and second connector are respectively coupled to the base.

In accordance with yet another example embodiment of the present disclosure a medical agent delivery system may comprise a delivery set including a base and a cannula which extends from the base for delivery of agent into a patient. The delivery set may include a set septum defining a fluid introduction volume in fluid communication with the cannula and otherwise sealed from the surrounding environment by the septum. The system may further comprise a medication delivery pump including an agent reservoir. The system may further comprise a tubing connector attached to a run of tubing in fluid communication with the agent reservoir. The tubing connector may include a first delivery member in fluid communication with the tubing and at least one first connection interface configured to couple to the delivery set. The system may further comprise a second connector including a second delivery member and at least one second connection interface configured to couple to the delivery set. The second connector may include an injection receiving volume in fluid communication with the second delivery member but otherwise sealed to the surrounding environment by injection septum.

In some embodiments, the pump may include a controller. The controller may be configured to govern operation of the pump to dispense agent according to a predetermine delivery prescription. In some embodiments, the injection septum may be constructed of a self-sealing material which forms a fluid tight seal after a sharp which has punctured the septum is removed. In some embodiments, the set septum may be constructed of a self-sealing material which forms a fluid tight seal after a sharp which has punctured the septum is removed. In some embodiments, the first delivery projection may be in fluid communication with the fluid introduction volume when the at least one first connection interface is engaged with the delivery set. In some embodiments, the second delivery projection may be in fluid communication with the fluid introduction volume when the at least one second connection interface is engaged with the delivery set. In some embodiments, the delivery set may include a delivery assembly which is coupled into a receptacle defined on the base. In some embodiments, each of the at least one first connection interface may be identical to a corresponding one of the at least one second connection interface. In some embodiments, the first and second delivery projections may be oriented parallel to the base when the tubing connector and second connector are respectively coupled to the base. In some embodiments, the first and second delivery projections may be oriented parallel to an axis of the cannula when the tubing connector and second connector are respectively coupled to the base.

In accordance with another example embodiment of the present disclosure a fluid delivery system may comprise a delivery set including a cannula and at least one access entry to an interior volume of the delivery set in communication with the cannula. Each of the at least one access entry may be sealed by a self-sealing barrier. The system may further comprise a tubing set including a run of tubing having a connector at one end and a set connector at an opposing end. The set connector may include a first delivery member in fluid communication with the tubing and at least one first coupling member configured to couple the set connector to the delivery set. The system may further comprise an injection connector including a second delivery member and at least one second coupling interface configured to couple to the delivery set. The injection connector may include an injection port in fluid communication with the second delivery member but otherwise sealed to the surrounding environment by injection septum. The first and second delivery members may be in fluid communication with the interior volume respectively when the set connector and injection connector are coupled to the delivery set.

In some embodiments, the delivery set may include a delivery assembly which is coupled into a receptacle defined on a base of the delivery set. The cannula and the interior volume may be part of the delivery assembly. In some embodiments, each of the at least one first coupling interface may be identical to a corresponding one of the at least one second coupling interface. In some embodiments, the first and second delivery projections may be oriented parallel to a base of the delivery set when the set connector and injection connector are respectively coupled to the delivery set. In some embodiments, the first and second delivery projections may be oriented parallel to an axis of the cannula when the set connector and injection connector are respectively coupled to the delivery set. In some embodiments, the delivery set may include a first access entry and a second access entry. The first access entry may be aligned with the axis of the cannula and the second access entry may extend along an axis perpendicular to the axis of the cannula. In some embodiments, the injection connector may include an adapter guide configured to accept a delivery implement and guide a delivery sharp of the delivery implement through the injection septum.

In accordance with another example embodiment of the present disclosure a method of delivering agent from different sources to a delivery destination may comprise installing an infusion set such that a cannula of the infusion set is in fluid communication with the delivery destination. The method may further comprise coupling a tubing connector to the infusion set and placing a delivery projection of the tubing connector into fluid communication with an interior volume of the infusion set which fluidically communicates with the cannula. The method may further comprise delivering, under control of an infusion pump controller, fluid from and infusion pump to the tubing connector and into the delivery destination via the infusion set. The method may further comprise coupling a dedicated injection connector to the infusion set and placing a delivery projection of the dedicated infusion connector into communication with the interior volume. The method may further comprise advancing a delivery member of a delivery implement into an injection port of the dedicated injection connector and injecting fluid from the delivery implement into the delivery destination via the infusion set.

In some embodiments, the method further may comprise introducing the delivery implement into an adapter coupled to the dedicated injection connector. In some embodiments, the method further may comprise coupling an adapter to the dedicated injection connector. In some embodiments, connecting the tubing connector to the infusion set may comprise clipping the tubing connector to a portion of the infusion set. In some embodiments, coupling the dedicated injection connector to the infusion set may comprise clipping the dedicated injection connector to a portion of the infusion set. In some embodiments, placing the delivery projection of the tubing connector into fluid communication with the interior volume may comprise puncturing a septum of the infusion set and placing the delivery projection of the dedicated infusion connector into communication with the interior volume comprises puncturing the septum. In some embodiments, advancing the delivery member of the delivery implement into the injection port of the dedicated injection connector may comprise puncturing an injection septum of the dedicated injection connector. In some embodiments, the method may further comprise pausing delivery from the infusion pump and decoupling the tubing connector from the infusion set. In some embodiments, the method may further comprise recoupling the tubing connector to the infusion set and resuming delivery from the infusion set.

These and other aspects will become more apparent from the following detailed description of the various embodiments of the present disclosure with reference to the drawings wherein:

DETAILED DESCRIPTION

Figure 1:
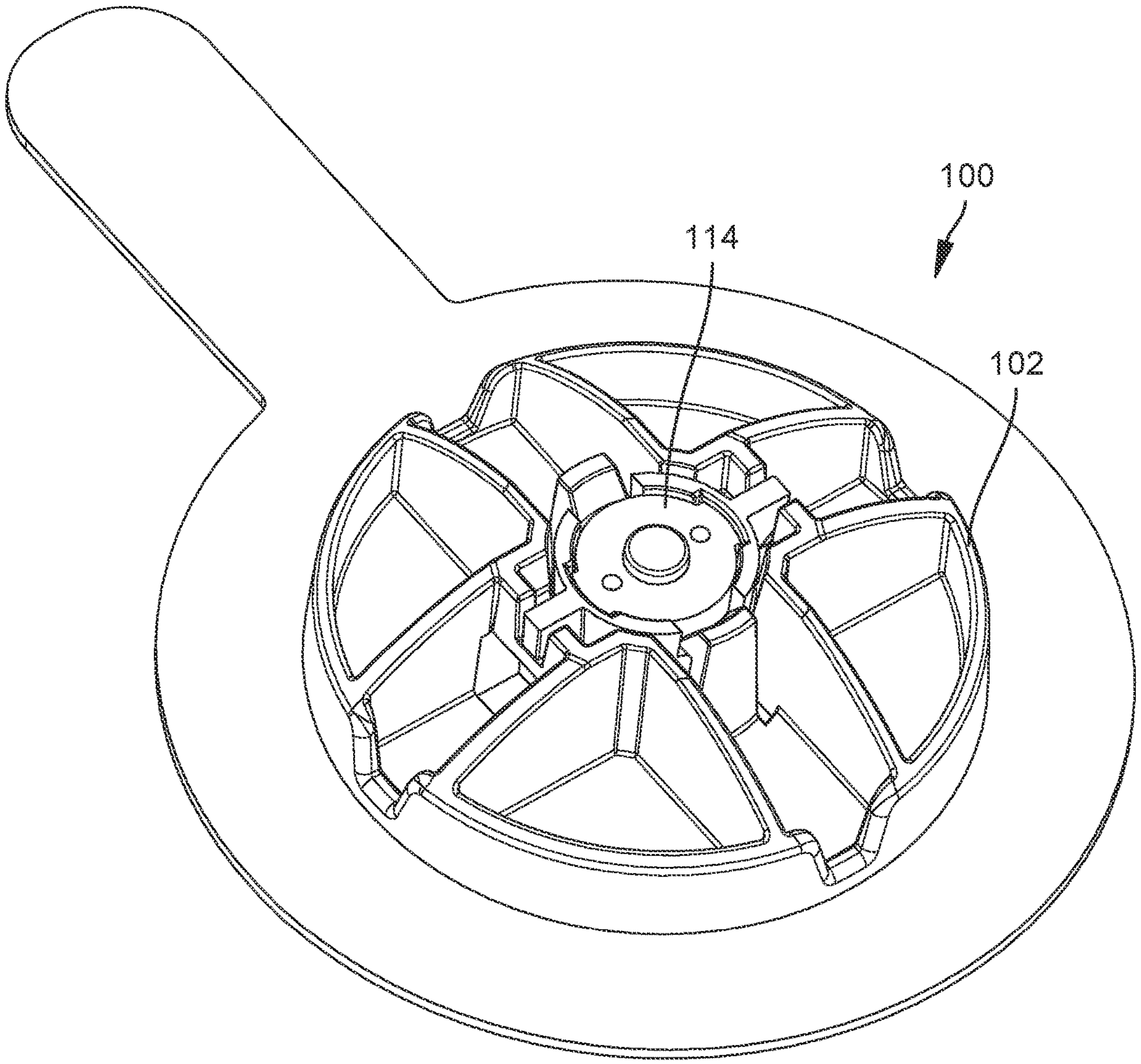
FIG. 1 depicts a perspective view of an example injection port assembly.

Referring now to FIG. 1, a perspective view of an exemplary injection port 100 is depicted. The example port 100 may be a low profile device which may be applied to the skin of a patient and provide a fluid delivery pathway into a delivery destination within the patient. The delivery destination may be a subcutaneous destination, intramuscular destination, or any other desired destination. Such a port 100 may be applied without the assistance of a physician or medical staff by a patient or caregiver with minimal training. The example port 100 may be sized to be coverable by clothing and contoured or shaped to aid in prevention of snags or bunching of any overlaying garments. Thus, a port 100 such as that shown in FIG. 1 may be easily concealed and present minimal inconvenience to a patient as they perform day to day activities.

Injection ports 100, such as the exemplary port 100 shown in FIG. 1, may be installed at a desired injection site and may be left in place on the skin for a prescribed period of time. The port 100 may have a fluid pathway which is sealed from the surrounding environment by a barrier, but accessible with a delivery sharp of a delivery implement. The fluid pathway may be contained within a delivery assembly 114. The delivery assembly 114 may couple to a support body 102 which may be mounted on an infusion site. It may be desirable that the port 100 be compatible with any delivery implement that the user may have previously used to self-inject an agent. Any suitable delivery implement may be used in various embodiments. Using diabetes as an example, a syringe or an injection pen used to perform daily injections of insulin may, for instance, be compatible with the injection port 100. Alternatively, various ports 100 may be arranged only to accept certain delivery implements which have been tailored for use with the port 100. In some embodiments, one or more adapter 250 (see, e.g., FIGS. 15-20) may be used in conjunction with a port 100 to facilitate interfacing of various delivery implements with the port 100.

The fluid pathway of the port 100 may be in fluid communication with the delivery destination in the patient. While the injection port 100 is in place, the user may interface a delivery implement with the port 100 to access a fluid pathway within the port 100. With the delivery implement in place, the user may initiate a delivery of fluid out of the delivery implement and into the injection port 100. As fluid is delivered into the injection port 100, the fluid may pass along the fluid pathway and to the delivery destination. The delivery implement may then be removed from the port 100 leaving the port 100 in place at the injection site. The barrier separating the fluid pathway from the surrounding environment may self-seal as the delivery sharp of the delivery implement is removed from the injection port 100.

During delivery of fluid to the delivery destination, the delivery sharp of the delivery implement may not contact the patient. Additionally, injection port 100 (and/or any adapter) may be constructed to help protect the patient from contact with the delivery sharp. Thus, the injection of agent into the patient via the injection port 100 may be conducted without puncture of the patient's skin with the delivery sharp. This consequentially avoids pain, discomfort, bruising, and scarring related to that particular delivery. Additionally, psychological concerns such as fear, stress, and/or anxiety may be averted when an agent delivery is administered via such an injection port 100.

Figure 2:
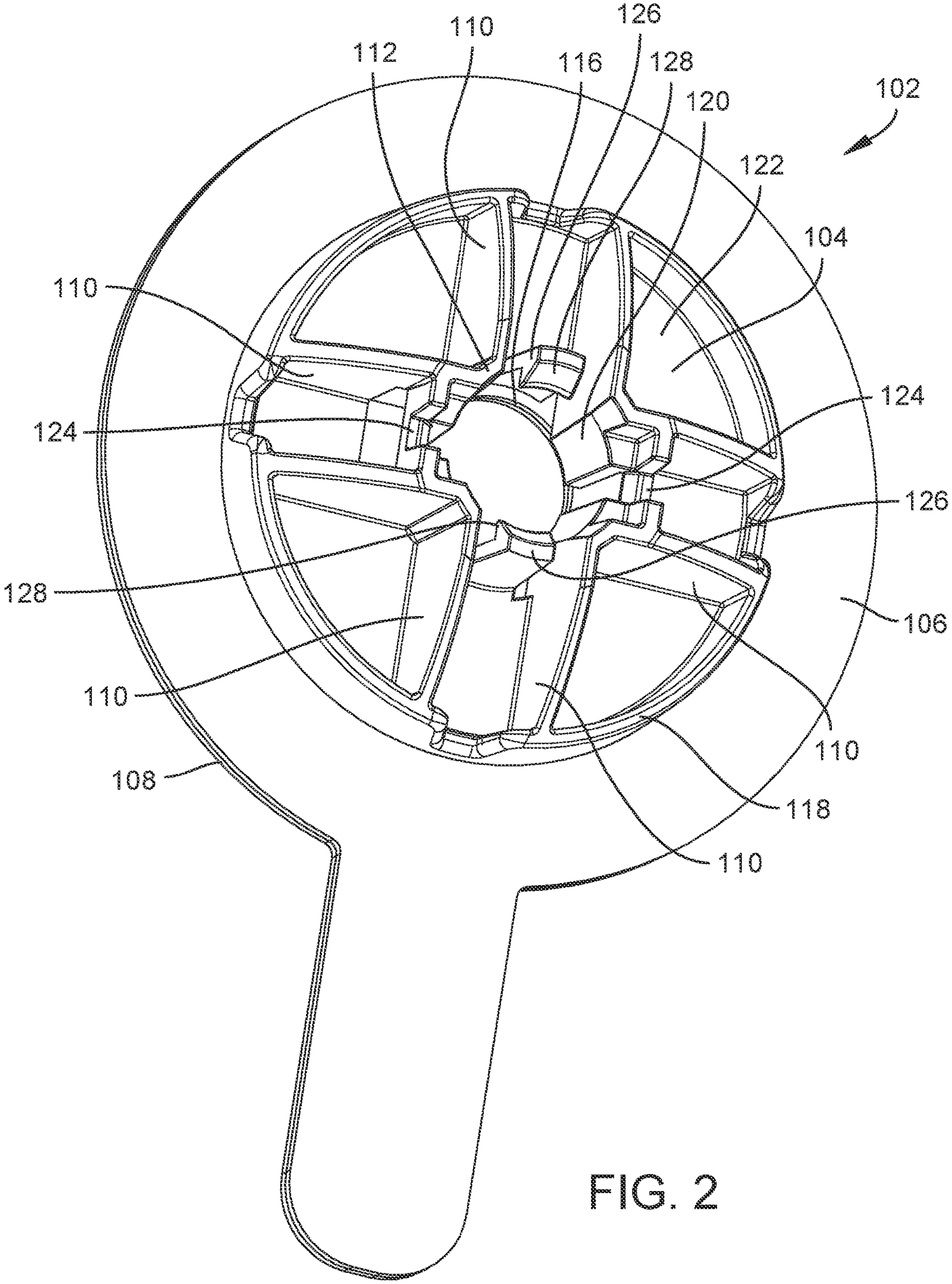
FIG. 2 depicts a perspective view of an example support body which may be included in an injection port assembly.

Referring now to FIG. 2, an injection port 100 (see, e.g., FIG. 1) may include at least two portions. One portion may be a delivery assembly 114 (see, e.g., FIG. 3-5) which may provide a sealed fluid pathway into the patient. The second portion may be a support body 102. An example support body 102 is depicted in FIG. 2. The delivery assembly 114 may couple to the support body 102 and remain coupled to the support body 102 during usage life of the injection port 100. The support body 102 may hold the delivery assembly 114 in place and may anchor the injection port 100 to the skin. The delivery assembly 114 may not be directly attached or adhered to the infusion site. In some embodiments, the delivery assembly 114 may couple to the support body 102 during placement of the injection port 100 at a desired infusion site (e.g. via an inserter assembly).

As shown in FIG. 2, the support body 102 may have a main body 104 which may be generally planar. Contoured main bodies 104 arranged to be placed at particular curvaceous regions of the skin are also possible. The main body 104 may have a round footprint (any other desired shape may be used). In certain example, the main body 104 may have an obround footprint for example.

The support body 102 may be positioned at a desired infusion site and retained in place by an adhering member 106. Such an adhering member 106 may include a substrate upon which a layer of skin compatible adhesive is applied. The adhering member 106 may be attached to a skin facing surface of the main body 104 in any suitable manner. In certain examples, an adhesive may be used to attach the adhering member 106 to the main body 104. In alternative embodiments, the adhering member 106 may be attached to the main body 104 via heat staking or welding (e.g. sonic, ultrasonic, RF). The adhering member 106 may be at least partially covered by a backing 108 which may, for instance, be made of a polymer or waxed paper material. The backing 108 may be placed over the adhesive of the adhering member 106 and may be removed prior to use in order to expose the adhesive of the adhering member 106.

The support body 102 may include a number of raised sections which may extend from and be proud of the main body 104. In the example embodiment, the raised sections are shown as ribs 110. The ribs 110 may strengthen the main body 104 and may facilitate molding of the support body 102. Ribs 110 may also help to bestow a smooth profile to the support body 110 which may help inhibit, for example, snagging, catching, or bunching up of clothing on the support body 102. In the example shown, pairs of ribs 110 are spaced at even angular intervals (substantially every 90°) on the support body 102. The support body 102 may include a receptacle 112 for mating with the delivery assembly 114 (see, e.g. FIGS. 3-5) of an injection port 100. The receptacle 112 may include a hole 116 which extends through the main body 104. When coupled in place, a patient contacting portion of the delivery assembly 114 may project though the hole 116 into a patient.

The ribs 110 may extend from the periphery of the support body 102 to the receptacle 112. A peripheral rim 118 may also be included and may be disposed along at least a portion (along the entirety in the example) the periphery of the support body 102. The peripheral rim 118 may aid in preventing contact of a delivery sharp with a patient. In the event that a user misses the delivery assembly 114, the delivery sharp may slide across the support body 102, but be confined by the peripheral rim 118. The peripheral rim 118 may thus help to inhibit a delivery sharp from sliding off the main body 104 and into contact with the skin. The ribs 110 may generally decrease in height as distance to the peripheral rim 118 decreases.

In the example, the receptacle 112 is generally centrally disposed on the support body 102 though need not be so in all embodiments. The receptacle 112 may include a receptacle wall 120 and the hole 116 may be surrounded, at least partially, by the receptacle wall 120. The receptacle wall 120 may project upwardly from the top face 122 of the main body 104. The receptacle wall 120 may include notches 124 which may be recessed into opposing sections of the receptacle wall 120. The notches 124 may be recessed into a portion of the receptacle wall 120 most distal to the main body 104. In some embodiments, the portion of the receptacle wall 120 most distal to the main body 104 may be tapered. The taper may facilitate installation of the delivery assembly 114 (see, e.g., FIGS. 3-5) into the receptacle 112 by funneling the delivery assembly 114 into place as the delivery assembly 114 is advanced into the receptacle 112. Additionally or alternatively, the notches 124 may be tapered along at least a portion of their length. For example, the section of the notches 124 most distal to the main body 104 may be tapered. Again, this may aid in guiding the delivery assembly 114 into place as the delivery assembly 114 is advanced into the receptacle 112.

The receptacle wall 120 may include at least one retainer member 126 which may capture and retain a delivery assembly 114 in place within the receptacle 112. The retainer member(s) 126 may be latching projections which may each engage a cooperating engagement region on the delivery assembly 114. The at least one retainer member 126 may be cantilevered so as to be resiliently deflected as the delivery assembly 114 is introduced.

Opposing break regions in the receptacle wall 120 may be included. Retainer member(s) 126 may extends from the top face 122 of the main body 104 within at least one of the break regions. In the example shown, multiple retaining members 126 are included with one retaining member 126 in each break region. The retaining members 126 are disposed in opposition to one another on opposite sides of the receptacle wall 120. Each retaining member 126 is disposed between the ribs 110 of an associated set of ribs 110. In certain examples, the retaining members 126 may be cantilevered from their connection point to the main body 104. Each retaining member 126 may include a protuberance (e.g. barb or ramp) 128 which may be disposed at its unsupported end. The protuberance 128 may project from the retaining member 126 into the receptacle 112.

Figure 3:
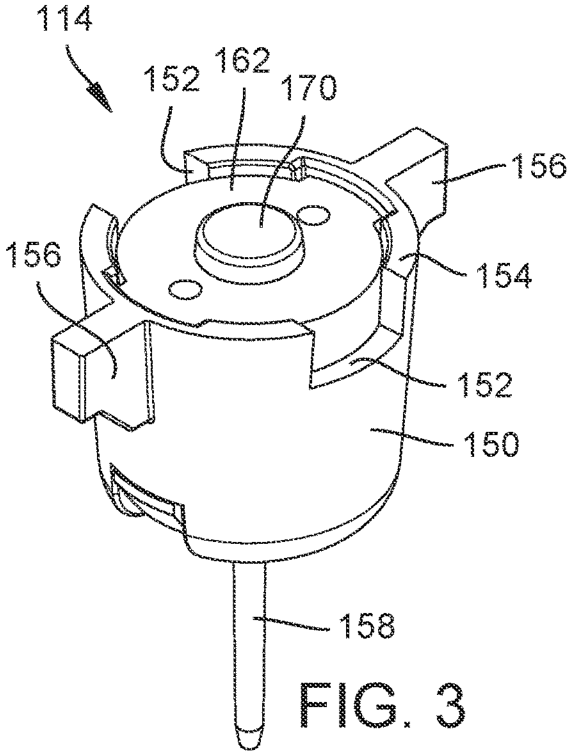
FIG. 3 depicts a perspective view of an example delivery assembly which may be included in an injection port assembly.
Figure 5:
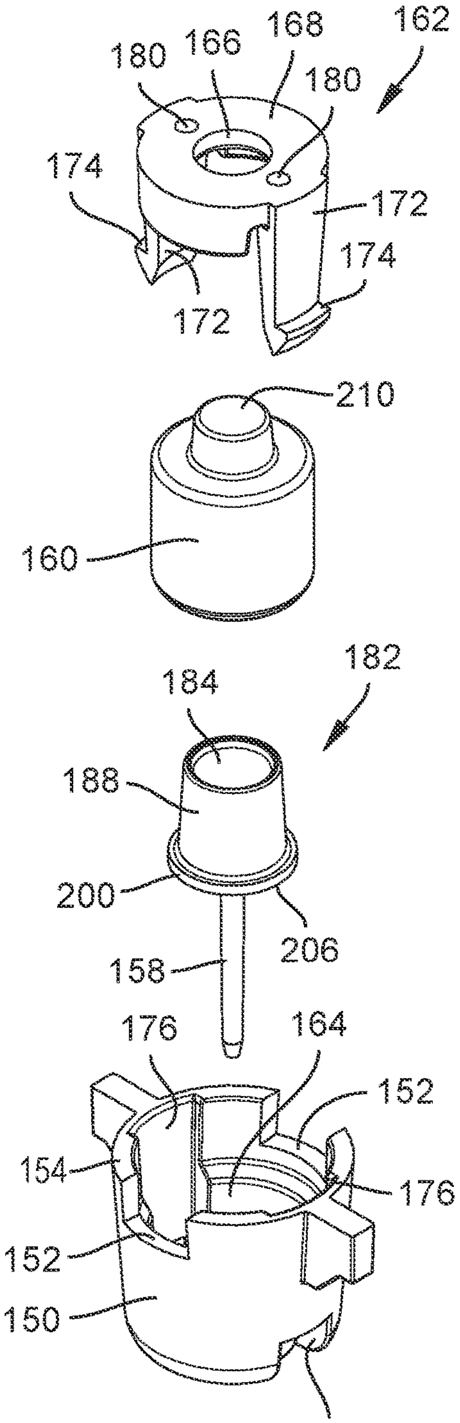
FIG. 5 depicts an exploded view of the example delivery assembly of FIG. 3.
Figure 4:
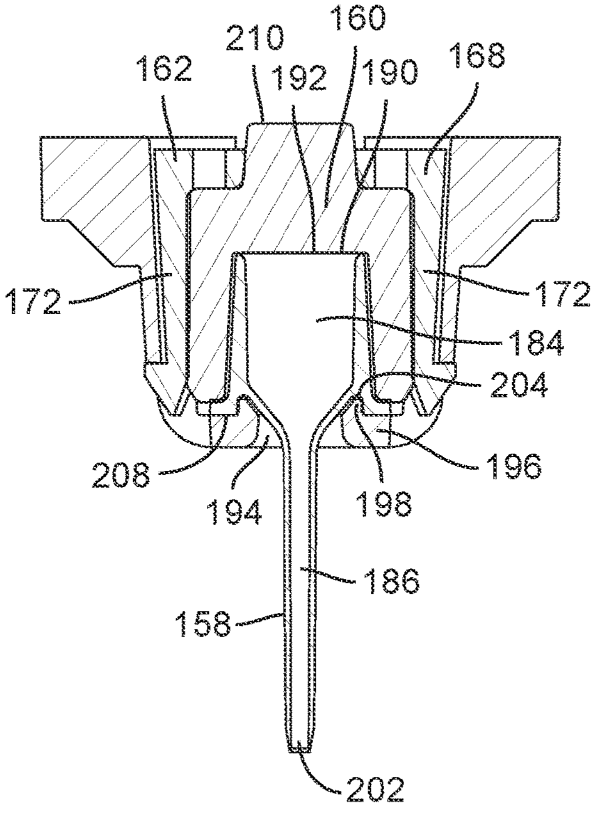
FIG. 4 depicts a medial cross-sectional view of the example delivery assembly shown in FIG. 3.

Referring now also to FIGS. 3-5, an example delivery assembly 114 is depicted. As shown, the delivery assembly 114 may include a housing 150 which may include at least one notch 152. The at least one notch 152 may be recessed into a top face 154 of the housing 150. As shown, two notches 152 diametrically opposed to one another are included. During displacement of the delivery assembly 114 into the receptacle 112 of the support body 102 (see, e.g., FIG. 2), the retainer member(s) 126 (see, e.g., FIG. 2) may deflect around the housing 150 until the protuberance(s) 128 (see, e.g., FIG. 2) are free to spring into an associated notch 152. Once the retaining member(s) 126 have restored to an undeflected state and the protuberance(s) 128 are engaged with a respective notch 152, the delivery assembly 114 may be retained within the support body 102. In the retained state, ears or nubs 156 of the housing 150 may at least partially reside within the notches 124 of the support body 102.

Still referring to FIGS. 3-5, the delivery assembly 114 may include a cannula 158. The cannula 158 may extend into the skin of the patient to a delivery destination when the injection port 100 is in place at an injection site. The cannula 158 may extend into subcutaneous tissue in some examples though the cannula 158 could extend into an intramuscular delivery destination in certain embodiments. The cannula 158 may be a soft and/or flexible cannula 158. In some embodiments, the cannula 158 may be constructed of a polymer material. Embodiments utilizing a rigid or metallic cannula 158 are also possible. In certain embodiments, the cannula 158 may be molded integrally with the housing 150. In the example embodiment, the cannula 158 and the housing 150 are depicted as separate discrete components. The delivery assembly 114 may further include at least one barrier element 160 and a retainer 162 in certain embodiments. The housing 150 may include a bay 164 into which the barrier element 160 may be introduced. Once the at least one barrier element 160 is installed within the bay 164, the retainer 162 may be engaged with the housing 150 to capture the barrier element 160 in place within the delivery assembly 114. The barrier element 160 may be a septum as shown in the example embodiment. Such a septum may be constructed of an elastomeric material which may self-seal when punctured by a sharp or leak proof (at least up to a predefined pressure) after a sharp is withdrawn subsequent a puncture. Potential materials may include silicones for example. In other embodiments, the barrier element 160 may be a membrane which may be self-sealing when punctured by a sharp or leak proof (at least up to a predefined pressure) after a sharp is withdrawn subsequent a puncture.

The retainer 162 may include a main section 168. The main section 168 may be substantially flat and may have a shape which corresponds to the cross-sectional shape of the bay 164. Thus, the main section 168 may be at least partially seated within the bay 164 when capturing the barrier element 160 within the housing 150. The retainer 162 may also include at least one cantilevered projection 172 extending therefrom. In the example embodiment two cantilevered projections 172 are included and are disposed in opposition to one another on the main section 168. At an unsupported end of each cantilevered projection 172 there may be a catch 174.

As the retainer 162 is assembled into the delivery assembly 114, the cantilevered projections 172 may engage with respective guide tracks 176 defined within the bay 164 of the housing 150. The guide tracks 176 may begin at the top face 154 of the housing 150 and terminate at respective apertures 178 defined in the wall of the housing 150. The guide tracks 176 may direct the cantilevered projections 172 as the retainer 162 is displaced toward the housing 150. The guide tracks 176 may be spaced such that the cantilevered projections 172 may be deflected toward one another when the cantilevered projections 172 are engaged with the guide tracks 176. When the catches 174 of each cantilevered projection 172 reach the apertures 178, the cantilevered projections 172 may be free to restore to an undeflected state. Once restored to the undeflected state, the catches 174 may engage with an edge of the associated aperture 178 inhibiting removal of the retainer 162.

The barrier element 160 may include a single or sole portion which is accessible via a delivery sharp. The accessible portion of the barrier element 160 may be in line with the axis of the cannula 158. The accessible portion may be present in a face of the delivery assembly 114 which is spaced from the main body 104 and may perhaps be parallel to the main body 104. As shown, the main section 168 of the retainer 162 may include a channel 166 which extends therethrough. The example channel 166 is disposed in substantially the center of a main section 168 of the retainer 162. When the retainer 162 is coupled in place in the delivery assembly 114, a nub or projection 170 of the barrier element 160 may extend into the channel 166. This may be the only portion of the barrier element 160 which is exposed on the exterior of the delivery assembly 114.

In some embodiments, there may be additional small passages 180 through the main section 168 of the retainer 162. No portion of the barrier element 160 may project through these small passages 180. These small passages 180 may be provided to aid in manufacturing.

The example cannula 158 may include an enlarged end region 182. The enlarged end region 182 may define an injection receiving volume 184 which may be continuous with the walls of a lumen 186 of the cannula 158. As discussed in greater detail later in the specification, the injection receiving volume 184 may accept the tip of a delivery sharp 270 (see, e.g., FIG. 16) of, for example, a syringe, injector pen, auto-injector, or other delivery implement 277 (see, e.g., FIG. 16). The enlarged end region 182 may also include a sealing surface 188 disposed on its exterior face surrounding the injection receiving volume 184. An interior wall 190 of the barrier element 160 may seal against the sealing surface 188 in fluid tight manner. The sealing surface 188 may have a number of different geometries depending on the embodiment though is substantially straight walled in the example shown. The barrier element 160 may be compressed to some degree when in place within the housing 150 and captured by the retainer 162. The enlarged end region 182 may be sufficiently rigid to resist deformation due to compression of the barrier element 160.

When a delivery assembly 114 is assembled, all but one face of interior wall 190 of the barrier element 160 may be fluidically sealed against the sealing surface 188 of the cannula 158. The face 192 which does not form a seal against the sealing surface 188 may be disposed substantially normal to the axis of the cannula 158. To place an outlet of a delivery implement into fluid communication with the injection receiving volume 184, a delivery sharp of the delivery implement may puncture through the nub 170 and the face 192.

Preferably, the delivery sharp may be advanced through the barrier element 160 at an angle substantially perpendicular to the exposed face 210 of the nub 170. The channel 166 and nub 170 may be sized to present a small target for the delivery sharp. This may inhibit a delivery sharp from entering the barrier element 160 at an angle substantially different than perpendicular. As a result, the delivery sharp may be restricted by the channel 166 from advancing into a space other than injection receiving volume 184.

The housing 150 may include a passage 194 which extends through the bottom wall 196 of the housing 150. A seat 198, which may be a raised wall surrounding the passage 194, may also be included in the housing 150. As shown, the cannula 158 may include a flange 200 at an end of the enlarged end region 182 most proximal the outlet 202 of the cannula 158. A recess 204 may be defined in the face of the flange 200 most proximal the outlet 202. The recess 204 may accept at least a portion of the seat 198 and may aid in locating and retaining the cannula 158 in place within the delivery assembly 114. The bottom face 206 (that most proximal the outlet 202 of the cannula 158) of the flange 200 may rest against the bottom wall 196 of the housing 150. In some examples, the bottom wall 196 of the housing 150 may include a receptacle 208 into which the flange 200 may be placed. When the delivery assembly 114 is assembled, the cannula 158 may extend through the passage 194 such that the outlet 202 of the cannula 158 is external to the housing 150.

A volume may be present between the exterior of the cannula 158 and the side walls of the passage 194. This volume may provide room for the cannula 158 to displace relative to the support body 102 (see, e.g., FIG. 1) if the injection port 100 or a portion of the patient's body causes a force to be applied to the cannula 158. This may minimize shearing action on the cannula 158. Additionally, this volume may serve as a volume into which an agent may be placed. Any suitable agent may be used. For example, an antimicrobial agent, analgesic agent, or anti-inflammatory agent may be placed in this volume.

Referring now to FIGS. 6-10 to place an infusion port 100 at an infusion site an inserter assembly 400 may be used. The injection port 100 may not be assembled when stored in an inserter assembly 400 awaiting use. The delivery assembly 114 and support body 102 may, for example, be separate. When an inserter assembly 400 is triggered, the delivery assembly 114 may be coupled to the support body 102 during the actuation sequence of the inserter assembly 400. For example, delivery assembly 114 may be driven toward the support body 102. As this occurs, the retainer member(s) 126 (see, e.g., FIG. 2) of the support body 102 may deflect around the housing 150 (see, e.g., FIG. 3) of the delivery assembly 114 until the protuberance(s) 128 (see, e.g., FIG. 2) are free to spring into an associated notch 152 (see, e.g., FIG. 3) of the housing 150.

Certain inserter assemblies 400, such as that shown in FIGS. 6-10, may be placed on the skin 500 and be designed to prevent actuation until the skin 500 has been displaced from its normal, resting position on the body. Actuation of an inserter assembly 400 may be precluded until some degree of displacement of the skin 500 has occurred. Actuation of an inserter assembly 400 may be prohibited until a certain amount of relative displacement between components of an inserter assembly 400 has occurred. This relative displacement may be effected as the skin 500 is lifted and the inserter assembly 400 is withdrawn away from the patient. The adhesion of the adhering member 106 of the support body 102 to the skin 500 may cause certain components (e.g. at least one component coupled to the support body 102) to be restricted in their displacement as the user withdraws the inserter assembly 400. As the inserter assembly 400 is withdrawn, the elasticity of the skin 500 may exert a force on the support body 102 (and any coupled component) pulling it toward or holding it closer to the patient. At least one other component of the inserter assembly 400 may be free to displace or have greater freedom to displace as the inserter assembly 400 is removed. Relative movement may, in certain examples, be inhibited until a certain force is exerted against the support body 102 by the skin 500. A trigger for the inserter assembly 400 may be kept from actuation until the skin 500 has been tugged away from the rest of the body a distance sufficient to generate the force required to begin relative movement. Triggering may not be possible until a requisite amount of relative displacement has occurred.

In some embodiments, inserter assemblies 400 may be placed on the skin 500 and trigger actuation as the inserter assembly 400 is lifted up so as to be removed. No other depression, twisting, squeezing, etc. of a trigger, button, housing sleeve or other portion of an inserter assembly 400 by a user may be needed to provoke the actuation, however, the actuation may still be under the control of the user. The relative movement of the free component(s) of the inserter assembly 400 with respect to the restricted component(s) may trigger actuation, by, for example, displacing or dislodging a latch and freeing one or more bias members to begin driving actuation. Thus, a trigger internal to the inserter assembly 400 may be actuated as a result of the removal action of the inserter assembly 400 from the body. From the perspective of a user, such an inserter assembly 400 may simply be placed on the skin 500 and then withdrawn to execute placement of the injection port 100.

While such designs may make triggering actuation simple, intuitive, and more foolproof, other advantages may also be realized. For example, as the inserter assembly 400 is lifted, the inserter assembly 400 may be designed so as to tug the skin 500 to which the support body 102 of the injection port 100 is attached away from the underlying muscle and other body structures. Thus, when inserted, the cannula 158 of the delivery assembly 114 may be more reliably placed within a subcutaneous layer of adipose tissue. This may reduce pain upon insertion, help minimize bruising, increase the potential body area over which infusion sites may be chosen, and may lead to more predictable absorption of agents such as insulin. The skin 500 may also be pulled taut facilitating easy penetration of the insertion sharp 402 through the skin 500. As the skin 500 is passively lifted along with the inserter assembly 400, no pneumatic vacuum is required to be generated. This may allow an inserter assembly 400 to be less complicated and made with fewer parts. Additionally, pneumatic seals either against the skin 500 or within the inserter assembly 400 may be omitted. Lifting of the skin 500 may be more reliably accomplished as the contour of the body at the infusion site (which could present a sealing challenge) may be largely irrelevant. Furthermore, no pinching of the skin 500 may be needed to pull the skin 500 away from the underlying structures. This may help to make the insertion more comfortable, may limit bruising, and may more reliably pull the skin 500 away from underlying structures. The inserter assembly 400 may also ensure that insertion of the cannula 158 into the skin 500 occurs at a prescribed orientation. The skin 500 may be held in place so as to be parallel or perpendicular to a reference plane or axis (e.g. parallel to the bottom face of the support body 102 of the injection port 100 or perpendicular to the axis of the insertion sharp 402 or insertion sharp displacement path) which moves with the inserter assembly 400. Thus, the angle of the inserter assembly 400 or path along which the inserter assembly 400 is pulled away with respect to the body may not alter insertion angle. Example embodiments shown herein depict an insertion angle which is substantially perpendicular to the skin 500, however, insertion at any angle (just over 0° to 90°, e.g. 30°, 45°, 60° etc.) may be similarly ensured by fixing the skin 500 relative to a reference plane or axis which moves with the inserter assembly 400. Another potential benefit is that there may be less psychological concern associated with the triggering of the actuation. As depression, twisting, squeezing, etc. of some actuator by the user may not be necessary, there may be less anxiety built up in anticipation of triggering the actuation. The exact moment of actuation as the inserter assembly 400 is withdrawn may not be known to the user. This may help to limit psychological concerns and may lower perceived pain.

Figure 6:
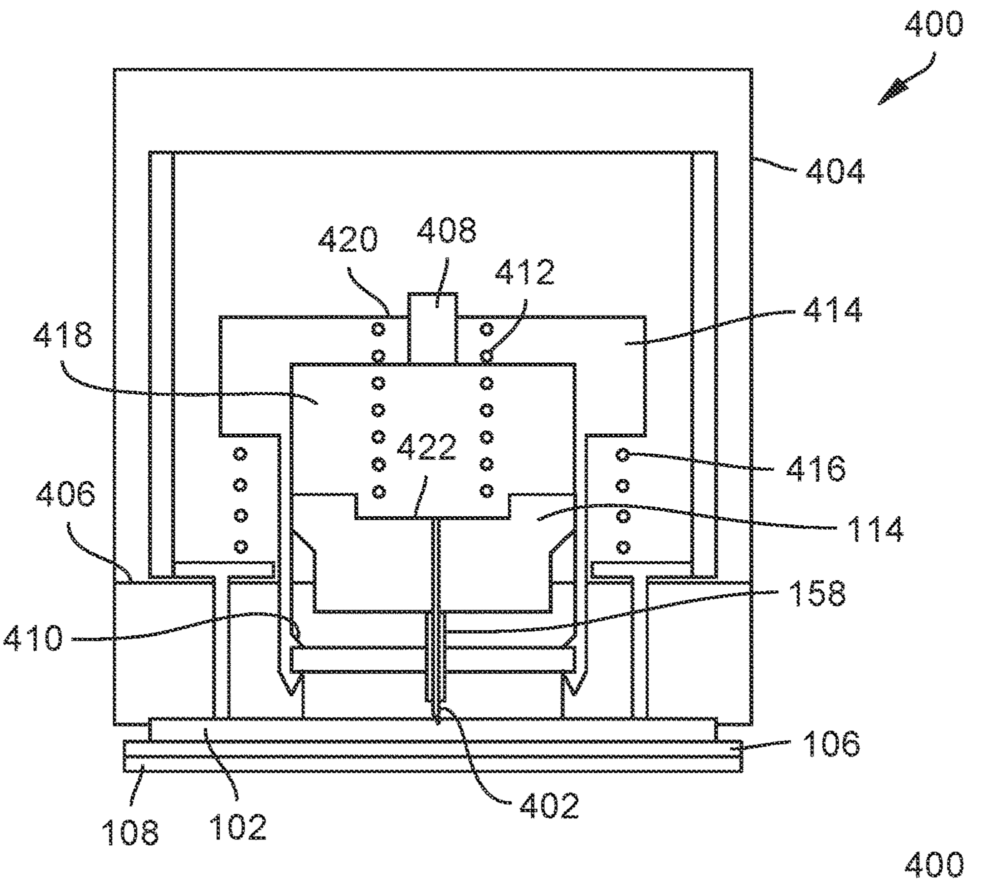
FIGS. 6-10 depict a number of representational diagrams depicting an exemplary inserter assembly which may be used to place an injection port assembly at an injection site.
Figure 7:
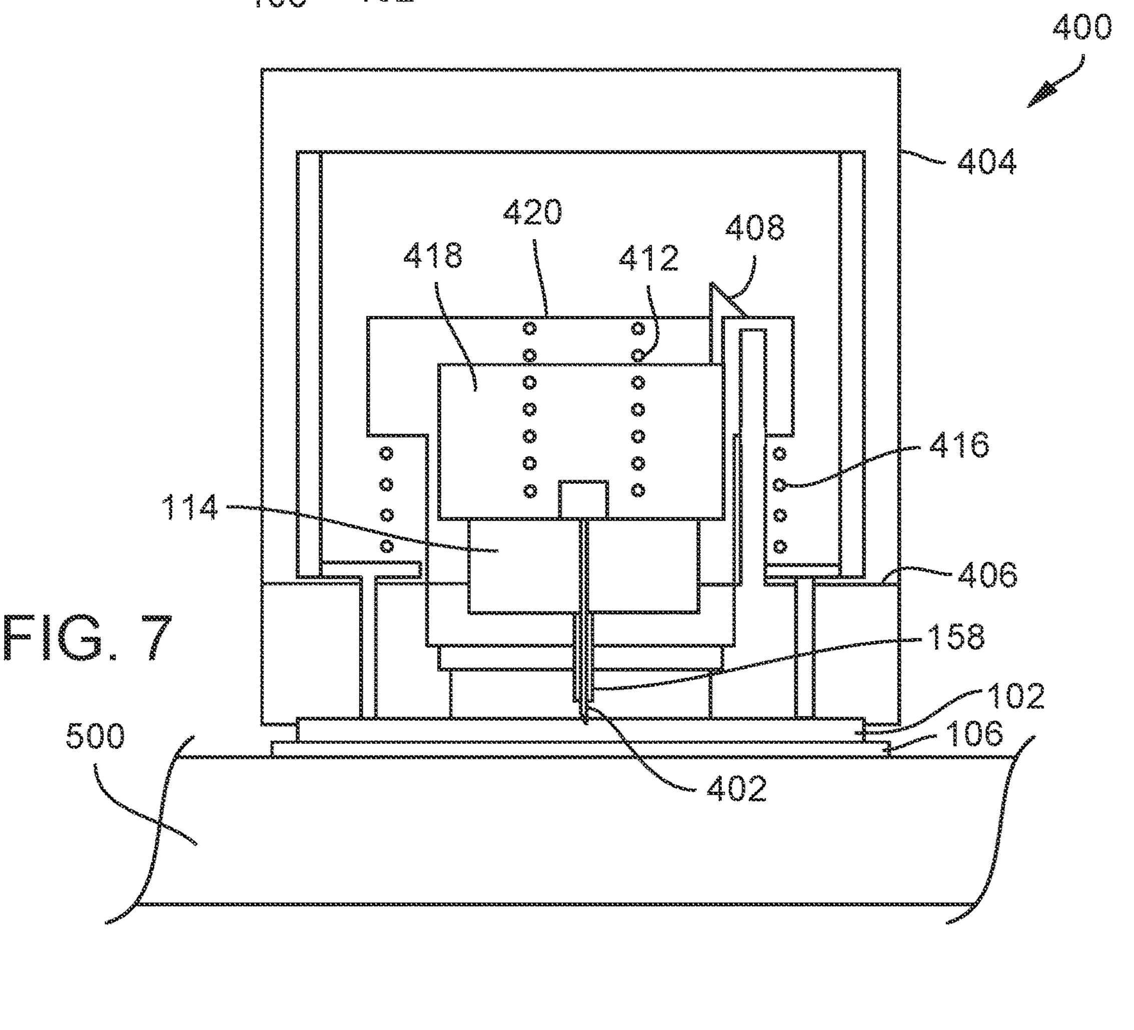
Figure 8:
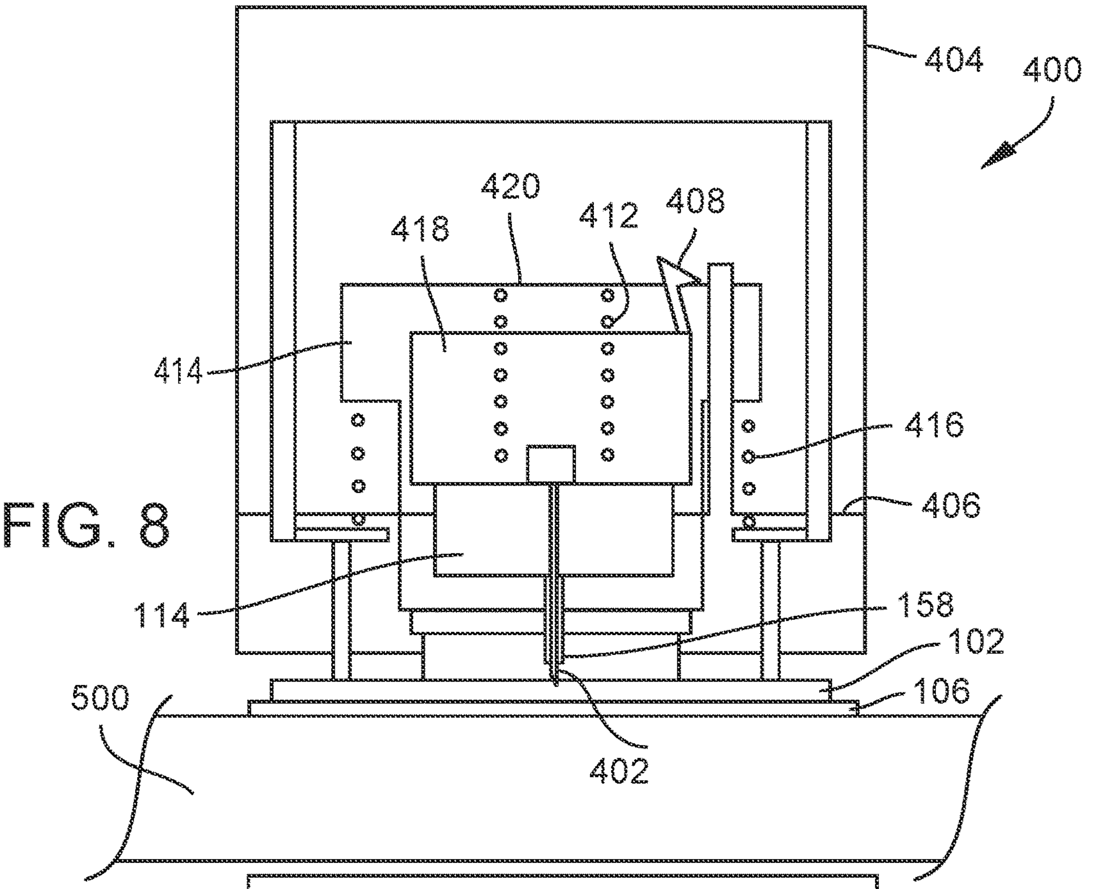
Figure 9:
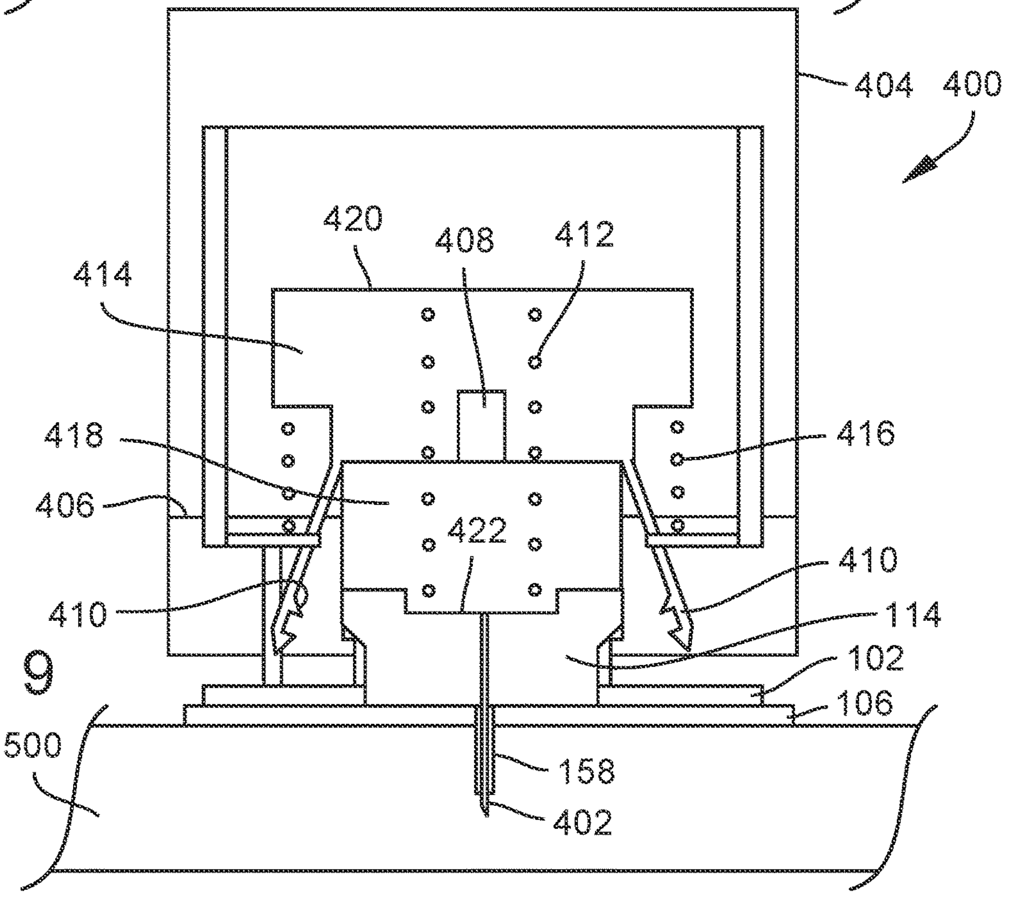
Figure 10:
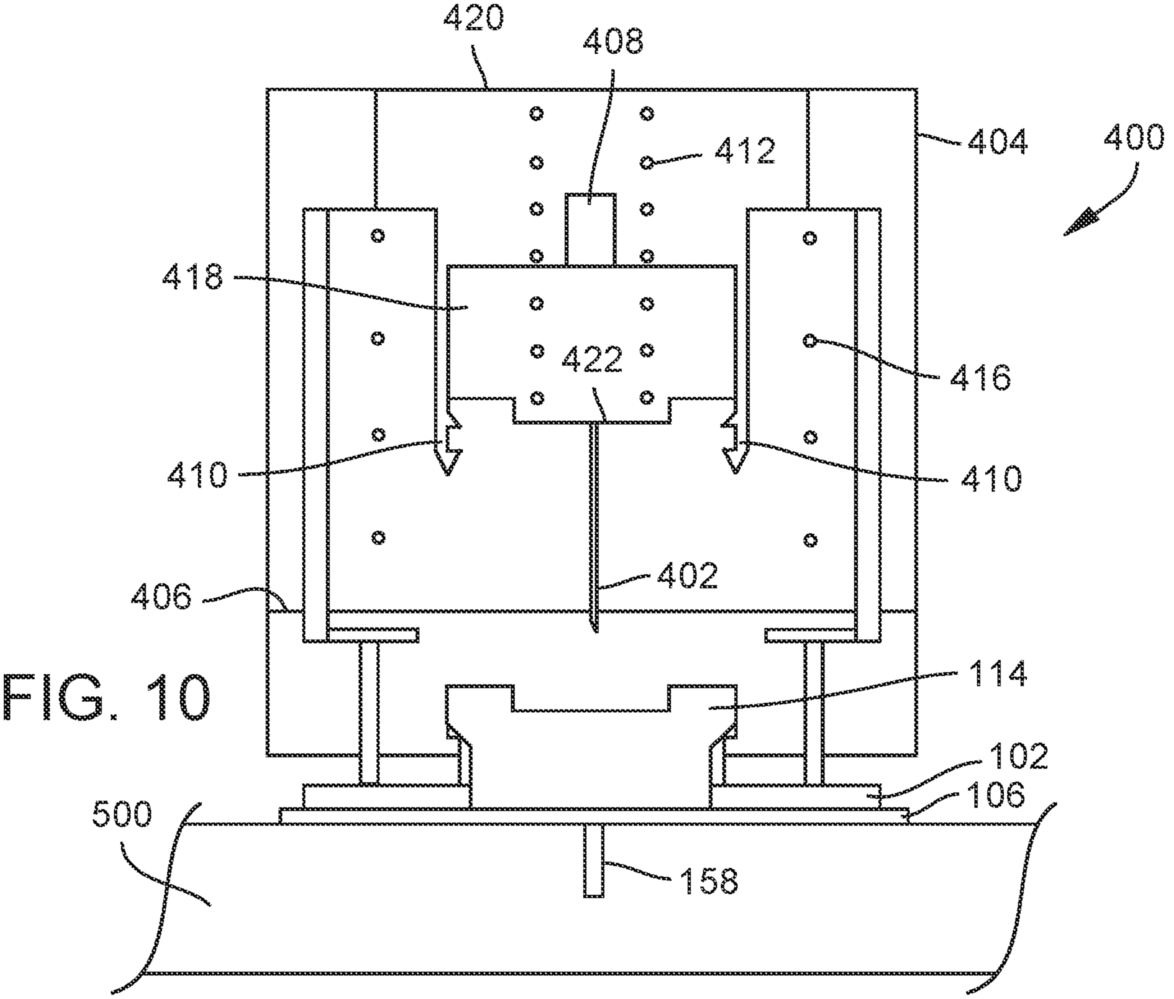

The progression of FIGS. 6-10 depicts an exemplary inserter assembly 400 actuation. It should be noted that each view shown in FIGS. 6-10 is a cross-sectional view taken along a midplane of the inserter assembly 400. FIGS. 6, 9, and 10 are taken along the same cut plane while FIGS. 7 and 8 are taken on a cut plane disposed perpendicular to the cut plane of FIGS. 6, 9 and 10. An adhesive liner or backing 108 (see, e.g., FIG. 6) may be removed from the support body 102 which may be retained within the inserter assembly 400. The inserter assembly 400 may then be placed on a desired infusion site (see, e.g., FIG. 7). This may cause the adhesive of the adhering member 106 to stick to the skin 500 of the patient. It may be desirable to press the inserter assembly 400 against the skin 500 to ensure a robust attachment of the adhesive to the skin.

The inserter assembly 400 may begin to be removed from the patient. This may lead the skin 500 to be tugged away from underlying muscle and body structures via the adhesion of the adhesive on the adhering member 106 (see, e.g., FIG. 8). A housing 404 and base member 406 may also be displaced relative to the rest of the inserter assembly 400. At least one latch 408 within the inserter assembly 400 may be released due to the relative displacement (see, e.g., FIG. 8). The latch 408 may hold a sharp bearing body 418 on which an insertion sharp 402 is borne in place against a compressed bias member 412. The bias member 412 may be captured between an end 420 of an insertion sharp retractor 414 and a wall 422 of the sharp bearing body 418. The insertion sharp 402 may extend through the delivery assembly 114 and project out of the cannula 158. Thus, the delivery assembly 114 may be carried on the insertion sharp 402.

The insertion sharp 402 and delivery assembly 114 may be driven together towards the insertion site once the latch 408 has been released as this may allow the bias member 412 to restore to an uncompressed state (as described below, the insertion sharp retractor 414 may be inhibited from displacing). The delivery assembly 114 may couple to the support body 102 after the delivery assembly 114 has been advanced toward the support body 102 beyond a certain distance. Additionally, at least one catch 410 may be released from the support body 102 when the delivery assembly 114 and support body 102 are coupled (see, e.g., FIG. 9).

The catch 410 may couple the insertion sharp retractor 414 to the support body 102 and inhibit movement of the insertion sharp retractor 414 relative to the support body 102. With the catch 410 released, the insertion sharp retractor 414 may able to be driven away from the support body 102 by a second bias member 416 (see, e.g., FIG. 10). The second bias member 416 may be freed to restore to an uncompressed state when the catch 410 is released. A mechanical interference which prevents dissociation of the sharp bearing body 418 and the insertion sharp retractor 414 may be present. Due to this interference, the sharp bearing body 418 may be pulled away from the now assembled injection port 100 as the insertion sharp retractor 414 is urged into the housing 400 by the second bias member 416. Thus when the inserter assembly 100 actuation has completed, the injection port 100 may be fully assembled and in place on the infusion site. The cannula 158 may be in place in the subcutaneous layer of skin. The insertion sharp 402 may also be retracted into the housing 402 and inaccessible to the user.

Figure 11:
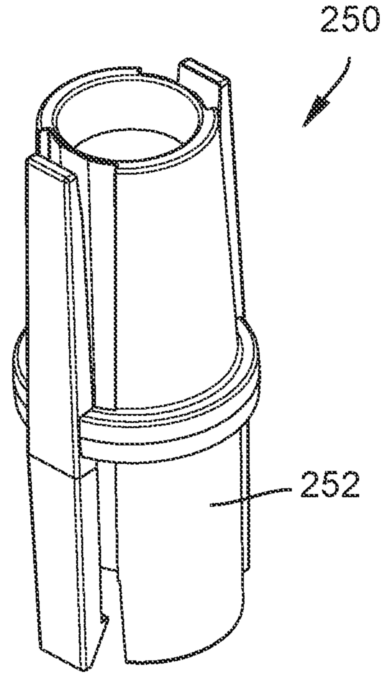
FIG. 11 depicts a perspective view of an example adapter.
Figure 12:
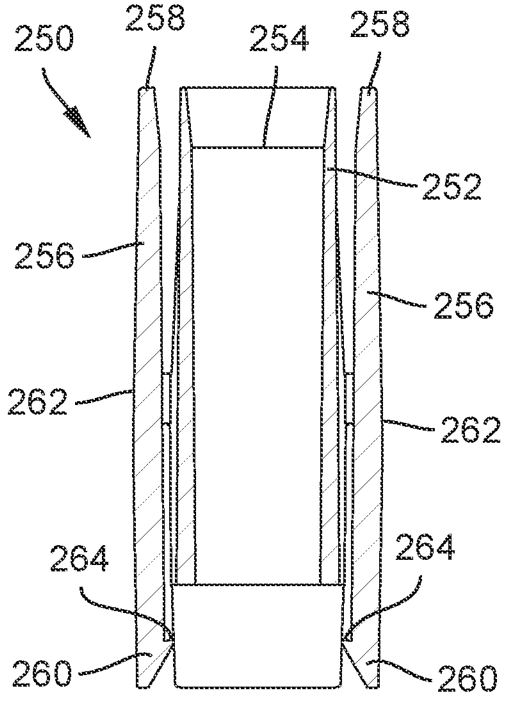
FIG. 12 depicts a medial cross-sectional view of the example adapter depicted in FIG. 11.

Referring now to FIGS. 11-12, an example adapter 250 is depicted. Though various embodiments of injection ports 100 may be directly accessed via a delivery implement 277 (see, e.g., FIG. 16), an adapter 250 may be provided with certain embodiments. In some embodiments, an adapter 250 may be optional and utilized at the discretion of a patient. Patients with lower dexterity may, for example, elect to use such an adapter 250. Such an adapter 250 may aid in introducing a delivery sharp 270 (see, e.g., FIG. 16) into the delivery assembly 114 at a desired angle. Additionally, an adapter 250 may aid in centering a delivery sharp over a small puncture target (e.g. nub 170 of the barrier element 160). In some examples, the adapter 250 may also serve as a guard which may block access to the delivery sharp by a user. An adapter 250 may couple to the delivery implement (or may be an integral part of the delivery implement) and may releasably couple to a portion of the injection port 100 (e.g. support body 102).

The example adapter 250 shown in FIGS. 11-12, includes an elongate body 252. A bore 254 may be present in the elongate body 252 and may extend through the elongate body 252 substantially along the axis of elongation of the elongate body 252. The elongate body 252 may also include at least one flanking arm 256. In the example embodiment, two flanking arms 256 disposed on opposing sides of the elongate body 252 are included.

The arms 256 may be about the same length as the elongate body 252 though may be shorter or longer than the elongate body 252 in alternative embodiments. The flanking arms 256 may include a first end 258, a second end 260, and an intermediate region 262. The second end 260 of each arm 256 may include a catch 264 which extends from the arm 256 toward the elongate body 252. The intermediate region 262 may be attached to the elongate body 252. Displacement of the first ends 258 of the flanking arms 256 toward the elongate body 252 may shift the flanking arms 256 from a closed state to an open state in which the catches 264 have been displaced away from the elongate body 252.

Figure 13:
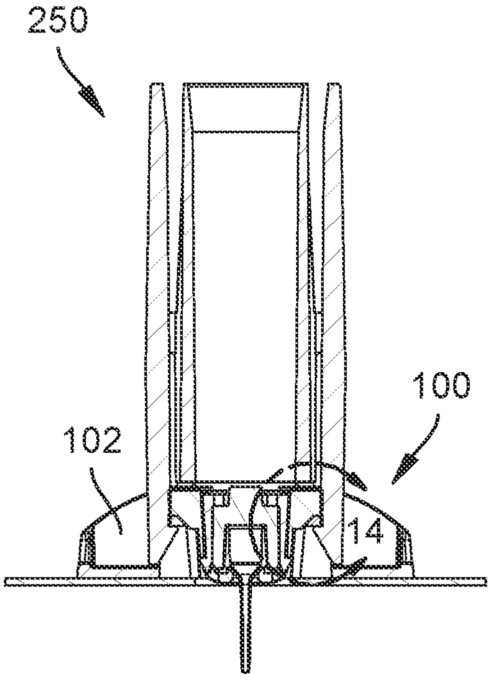
FIG. 13 depicts a cross-sectional view of an example adapter coupled to an example injection port assembly.
Figure 14:
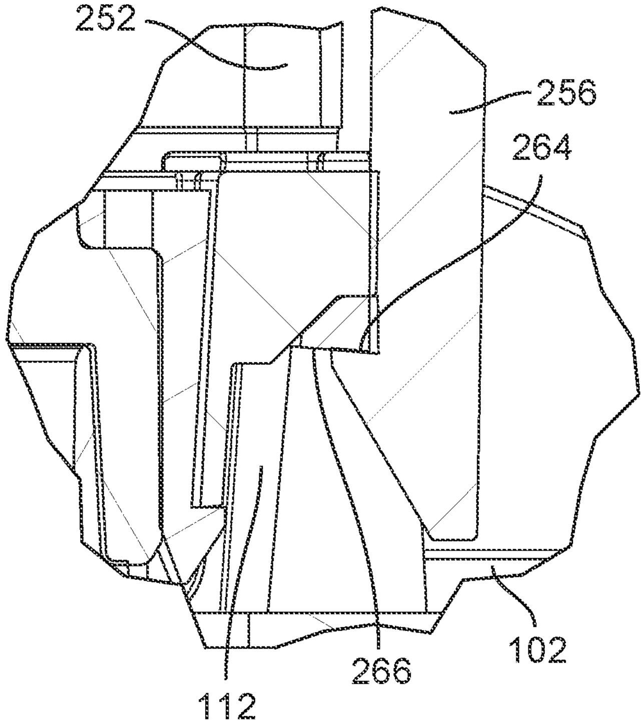
FIG. 14 depicts a detailed view of the indicated region of FIG. 13.

Referring now also to FIGS. 13-14, the adapter 250 may be coupled to the injection port 100. As shown, the catch 264 on each arm 256 of the adapter 250 may engage with a ledge 266 on the support body 102. In the example embodiment shown, the ledge 266 is defined in the wall of the receptacle 112 and is disposed in line with the notches 124 (see, e.g., FIG. 2). The catches 264 may each be associated a ramp which may aid in causing deflection of the arms 256 to the open state as the adapter 250 is pressed against the injection port 100. Once the catches 264 are advanced passed the ledge 266, the arms 256 may resiliently restore toward the closed position such that the catches 264 enter into engagement with the ledges 266 as shown best in FIG. 14. An end of the elongate body 252 may, in some examples, rest on the top face 122 (see. e.g. FIG. 2) of the main body 104 (see, e.g., FIG. 2) of the support body 102 when the catches 264 are in engagement with the ledges 266. The elongate body 252 may include slots which may accept any ribs 110 (see, e.g., FIG. 2) included on the support body 102. The first end 258 of the arms 256 may be pressed against the elongate body 252 to move the arms 256 to the open state in order to release the adapter 250 from the injection port 100.

Figure 15:
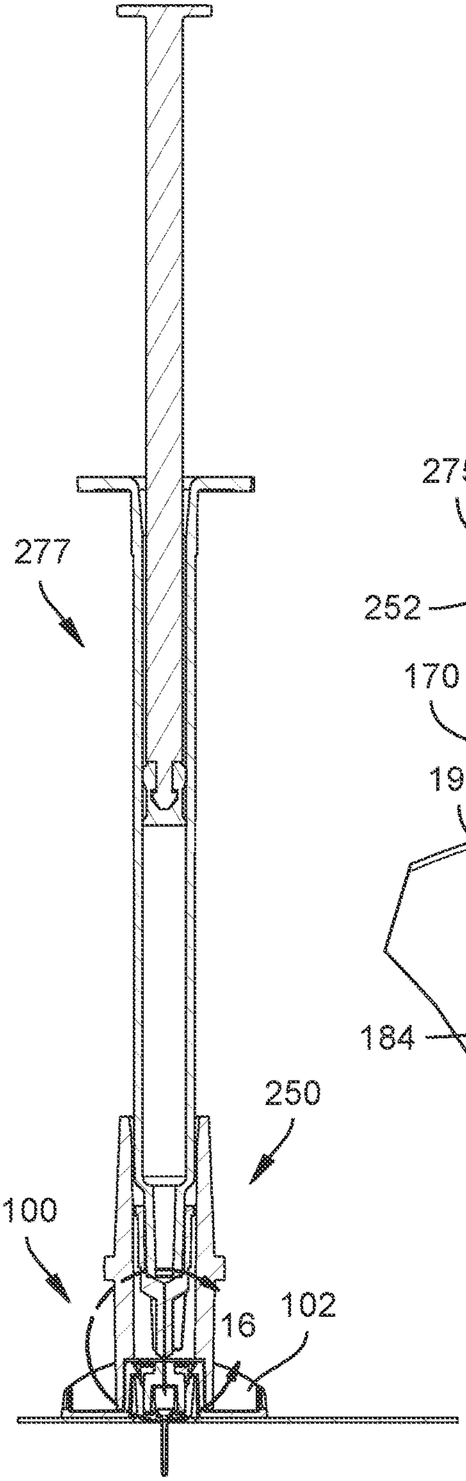
FIG. 15 depicts a cross-sectional view of an example adapter coupled to an example injection port assembly in which an example delivery implement has been advanced into fluid communication with an injection receiving volume of the injection port assembly.
Figure 16:
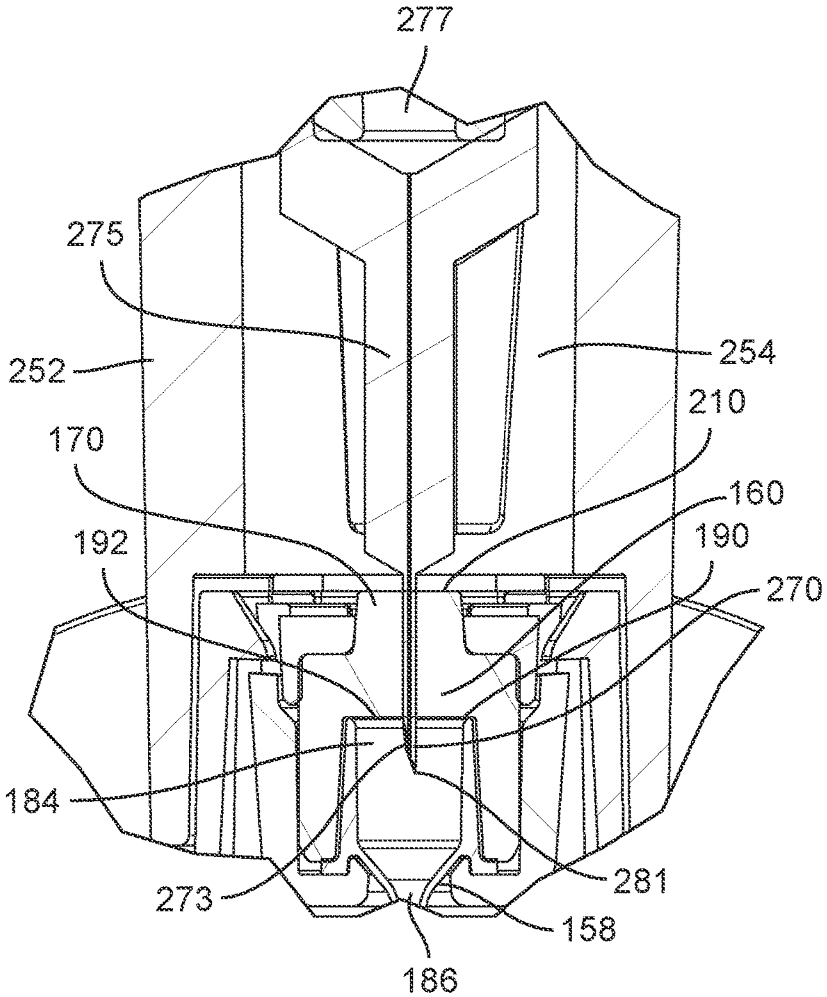
FIG. 16 depicts a detailed view of the indicated region of FIG. 15.

Referring now also to FIGS. 15-16, once the injection port 100 is in place on a patient (e.g. via an inserter assembly), an adapter 250 may be coupled to the support body 102. A delivery implement 277 may be introduced into the bore 254 of the elongate body 252. In some embodiments, the bore 254 may be sized such that a friction fit is generated as the delivery implement 277 is advanced into the bore 254. The delivery implement 277 may be a syringe in certain embodiments. In other embodiments, the delivery implement 277 may be an injection pen. In some embodiments, the delivery implement 277 may administer a preset or user selectable volume of agent. Any suitable delivery implement 277 may be used.

In some embodiments, the delivery implement 277 and bore 254 may include keying features (e.g. corresponding cross-sectional shapes not typical of standard syringes or the like) to ensure only an appropriate or prescribed delivery implement 277 may be utilized with the adapter 250. In some embodiments, the bore 254 of the elongate body 252 may be sized to accept delivery implements 277 up to a particular maximum fill volume. The bore 254 may have a size that prevents connection with delivery implements having, for instance, a wide diameter syringe barrel. In some alternative embodiments, the delivery implement 277 and adapter 250 may be integrated together and the adapter 250 may be fixedly attached or integral with a portion of the delivery implement 277. In such embodiments, the adapter 250 may also surround the delivery sharp 270 and may serve as a sharp guard. In some embodiments, the adapter 250 may irreversibly couple to the delivery implement 277. That is, the adapter 250 may couple to the delivery implement 277 in a manner in which manual separation of the two components would be impractically difficult or result in damage to one of the two components.

In the exemplary embodiment, a delivery implement 277 may be displaced into the bore 254. A delivery sharp 270 on the delivery implement 277 may pierce the nub 170 of the barrier element 160. The bore 254 may act as a guide which ensures that the delivery implement 277 will be appropriately aligned with the nub 170. The delivery implement 277 may be advanced into the bore 254 until a hub 275 for a delivery sharp 270 on delivery implement 277 contacts a portion of the injection port 100 (e.g. the delivery assembly 114). Alternatively, the bore 254 may include a stop (e.g. step or ledge) therein. The delivery implement 277 may include a surface which may abut such a stop and further displacement of the delivery implement 277 and the attached sharp 270 may be prevented.

In some embodiments, the first end 258 of the arms 256 may include a projection which may contact a delivery implement 277 in place in the adapter 250. In some examples, such a projection may only contact the delivery implement 277 when a user attempts to displace the first ends 258 against the elongate body 252. Thus, the delivery implement 277 may block displacement of the arms 256 to the open state. This may ensure that the adapter 250 is coupled to the injection port 100 before a delivery implement 277 is introduced to the adapter 250. Additionally, this may ensure that any delivery implement 277 is removed prior to the adapter 250 being decoupled from the injection port 100.

The delivery sharp 270 may be selected so as to have a length which prevents the delivery sharp 270 from contacting the cannula 158 or at least a portion of the cannula 158 (e.g. that including the lumen 186). The delivery sharp 270 may have a length which is greater than the distance between the exposed face 210 of the nub 170 and the face 192 of the interior wall 190 of the barrier element 160 (subsequently referred to as barrier distance). The delivery sharp 270 may have a length longer than the barrier distance by an amount equal to a partial percentage (e.g. 5-75%) of the injection receiving volume 184 height. Thus when the delivery sharp 270 is fully inserted into the delivery assembly 114, the outlet 273 of the delivery sharp 270 may be disposed within the injection receiving volume 184. The tip 281 of the delivery sharp 270 may also be spaced from the walls forming the lumen 186 of the cannula 158.

With the delivery sharp 270 in fluid communication with the injection receiving volume 184, the delivery implement 277 may dispense a volume of agent into the injection port 100. This agent may pass into a patient via the cannula 158 of the injection port 100. The delivery implement 277 and adapter 250 may then be removed from the injection port 100. The barrier element 160 material may self-seal as the delivery sharp 270 is removed. Thus, the sealed injection port 100 may be left behind at the injection site and used as desired or prescribed until a change of injection site is performed.

This may be particularly desirable for patients who perform frequent (daily or multiple daily) injections. A patient using an injection port 100 may only be punctured a single time by an insertion sharp each time an injection port 100 is placed at a desired infusion site. Agent may then be delivered through an injection port 100 without the need for additional punctures of a patient. Depending on the medications, it may also be possible to use a single injection port 100 for a variety of different medications. The injection port 100 may be left in place for perhaps a number of days before replacement and/or site change. This may save the user pain, anxiety, discomfort, or other suffering which would otherwise be associated with injections over the period of time the injection port 100 is left in place. Thus, use of such an injection port 100 may result in increased quality of life for the patient. Additionally, use of such an injection port 100 may lead to increased patient compliance with their treatment regimen as the associated pain and discomfort may be substantially eliminated.

Certain patients may receive a parenteral medication delivered under the control of an automated infusion pump. Such infusion pumps may be small enough to be carried by a patient and may be used to treat a variety of conditions. For example, such pumps may be utilized to deliver medication for diabetes (e.g. insulin, glucagon), hypertension (treprostinil), cancer (chemotherapy agents), etc. A run of tubing extending from a reservoir of the pump (or point in fluidic communication with the reservoir) to an infusion set 300 may be provided. The infusion set 300 may be placed at an infusion site and may provide a fluid communication pathway into a delivery destination within the patient. The pump may displace measured volumes of agent through the tubing and into the patient via the infusion set 300 to manage a condition of the associated patient. In certain scenarios, it may be desirable that the infusion set 300 be able to accept a manual injection from a delivery implement 277 in addition to a delivery from an infusion pump.

Figure 17:
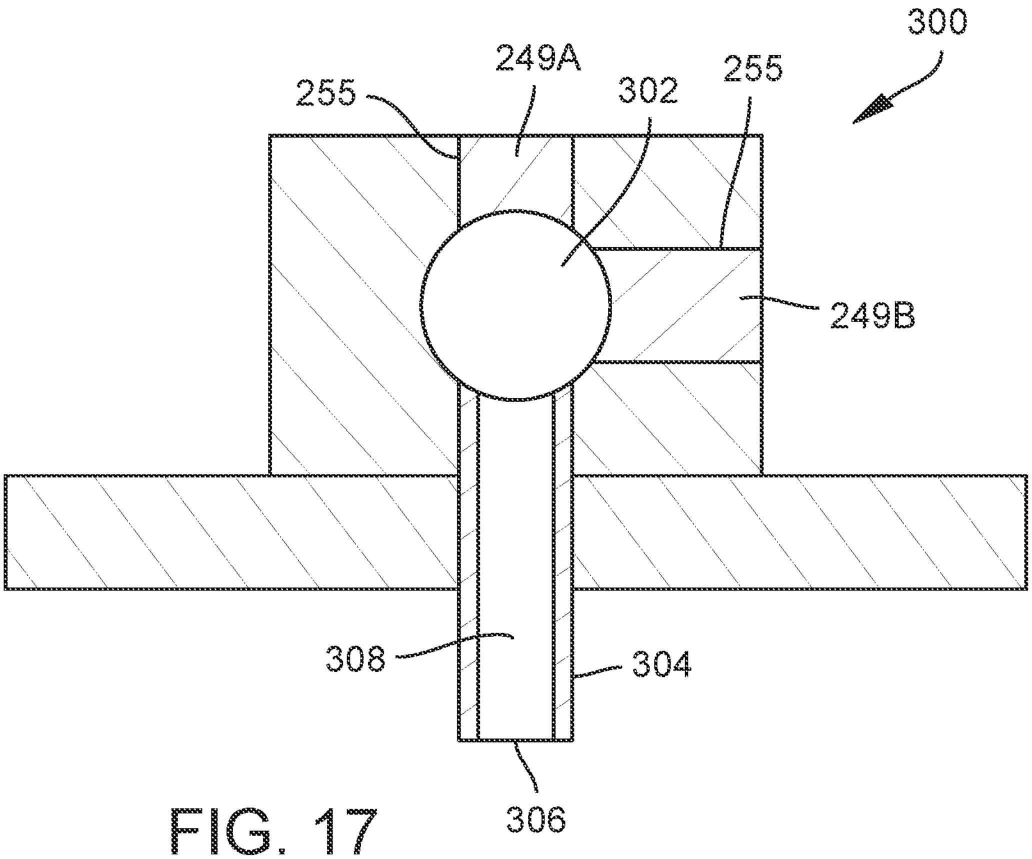
FIG. 17 depicts a view of an exemplary infusion set.

Referring now to FIGS. 17-22, an adapter 250 may be provided to allow infusion sets 300 to interface with a delivery implement 277. A diagram of an infusion set 300 is depicted in FIG. 17. The infusion set 300 shown in FIG. 17 is intended as an illustrative example. As further described below, any infusion set 300 may be used to deliver an injection dispensed from a delivery implement 277. As shown, an infusion set 300 may include an internal volume 302. The internal volume 302 may be in fluid communication with the patient via a dispensing body 304 such as cannula, a delivery sharp, metal needle, etc. extending from the rest of the infusion set 300. The internal volume 302 may be otherwise sealed from the environment and accessed through one or more sealing member 249A, B (e.g. membrane or septum). The sealing member(s) 249A, B may be positioned at access entries 255 through which fluid communication with the internal volume 302 may be established. Two discrete sealing members 249A, B are shown in the example, however, other embodiments may only include a single access entry 255 and associated sealing member 249A, B. Alternatively, a single sealing member 249A, B may be included and provide a seal at a plurality of access entries 255.

Where an infusion set 300 includes a soft or flexible cannula as a dispensing body 304, an insertion sharp may be used to facilitate puncture of the cannula into the skin. Puncture may be manual or automated by an inserter assembly. The insertion sharp may be attached to a body which is separate from the infusion set 300. The insertion sharp may extend through a sealing member 249A, along an axial direction of the cannula, through the lumen 308, and past the outlet 306 of the cannula. As the infusion set 300 is installed, the insertion sharp may puncture the skin making a path for the cannula. The insertion sharp may also support the cannula against bending or deflection as it is advanced into the patient. The insertion sharp may be removed subsequent placement of the infusion set 300 at the infusion site.

The tubing 251 leading to the infusion pump 293 may terminate in a tubing connector 263 (see, e.g., FIG. 20) at one end. The tubing 251 may include a connector 299 at the opposing end (e.g. a luer) which may mate with a cooperating connector 298 on a fluid conduit from the infusion pump 293. Alternatively, the tubing 251 may connect directly to an agent reservoir 233 of the infusion pump 293 or a portion of the infusion pump 293 in fluid communication with the reservoir 233. The tubing connector 263 may include a delivery projection 253 which may extend through any sealing member(s) 249A, B of the infusion set 300 and into communication with the internal volume 302. In the example, the tubing connector 263 includes a connector sharp. When the tubing connector 253 is coupled to the infusion set 300, the connector sharp may extend into communication with the internal volume 302 and pierce through any sealing member(s) 249A, B as needed to reach the internal volume 302. Other embodiments, may include a blunt delivery projection 253 which may open the sealing member(s) 249A, B (e.g. where the sealing member 249 is a split septum). The tubing connector 263 may couple to the infusion set 300 in any suitable manner. In some embodiments, the tubing connector 263 may include connector arms 287 (see, e.g., FIG. 20) which may clip onto the infusion set 300 and retain the tubing connector 263 in place on the infusion set 300.

Figure 20:
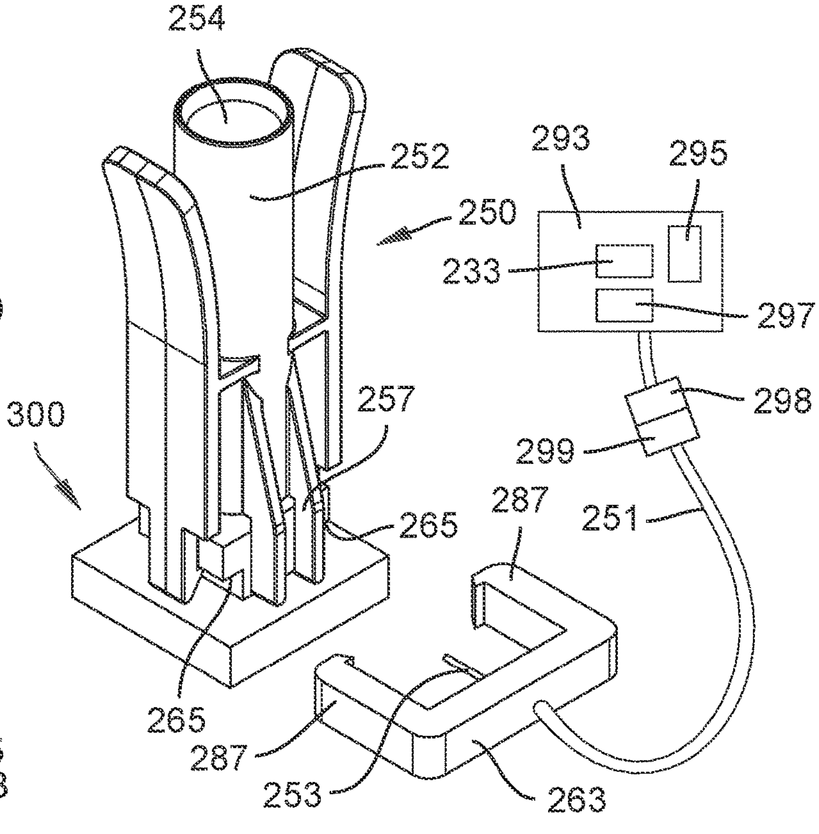
FIG. 20 depicts a view of an example adapter coupled to an example infusion set which is in fluid communication with an example infusion pump.

In some embodiments, a tubing connector 263 which connects the tubing 251 to the infusion set 300 may be removed to allow for coupling of an adapter 250 to the infusion set 300 (as shown in FIG. 20 for example). A controller 295 for the automated pump 293 may halt actuation of a delivery assembly 297 to pause fluid delivery from the pump 293 when the tubing connector 263 is decoupled from the infusion set 300. In other embodiments, an adapter 250 may be coupled to the infusion set 300 with the tubing connector 263 still in place. In still other embodiments, an adapter 250 may be coupled to the infusion set 300 through another component. For example, the adapter 250 may be coupled to the tubing connector 263 (see, e.g., FIG. 21-22) instead of the infusion set 300. In such embodiments, the adapter 250 may be used to dispense an injection into the infusion set 300 with the tubing connector 263 attached to the infusion set 300. Whether the tubing connector 263 is removed may depend upon the infusion set 300.

If the infusion set 300 includes a single access entry 255 to the interior volume, the tubing connector 263 may be removed in order to connect the adapter 250 and access the interior volume 302 via a delivery implement 277. Where multiple access entries 255 to the interior volume are included on the infusion set 300, the tubing connector 263 may remain in place when the adapter 250 is connected. For example, in some embodiments, the tubing connector 263 may include a delivery projection 253 which is oriented perpendicular to the axis of the dispensing member 304 when the tubing connector 263 is coupled to the infusion set 300 (see, e.g., FIG. 20). In such examples, a second access entry 255 in alignment with the axis of the dispensing projection 304 (e.g. that in which sealing member 249A is disposed within in FIG. 17) may be present to accommodate use of an insertion sharp as described above. This second access entry 255 may be left unobstructed when the tubing connector 263 is in place and available to be used to access the internal volume 302.

Figure 19:
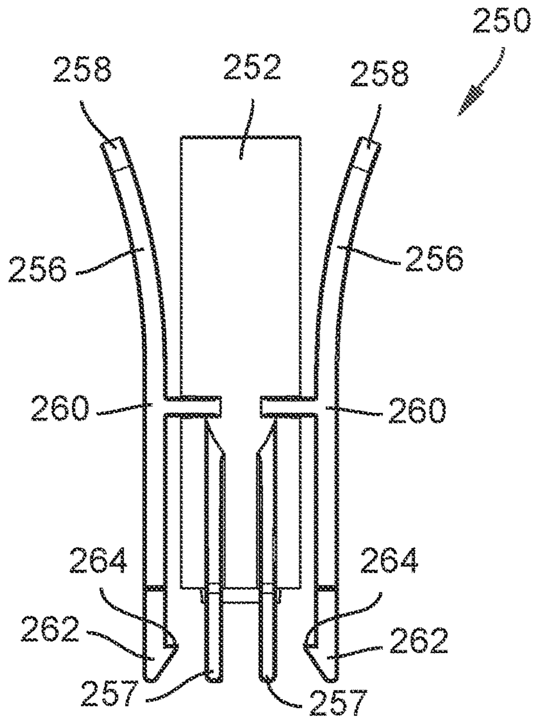
FIG. 19 depicts a front view of an example adapter.
Figure 18:
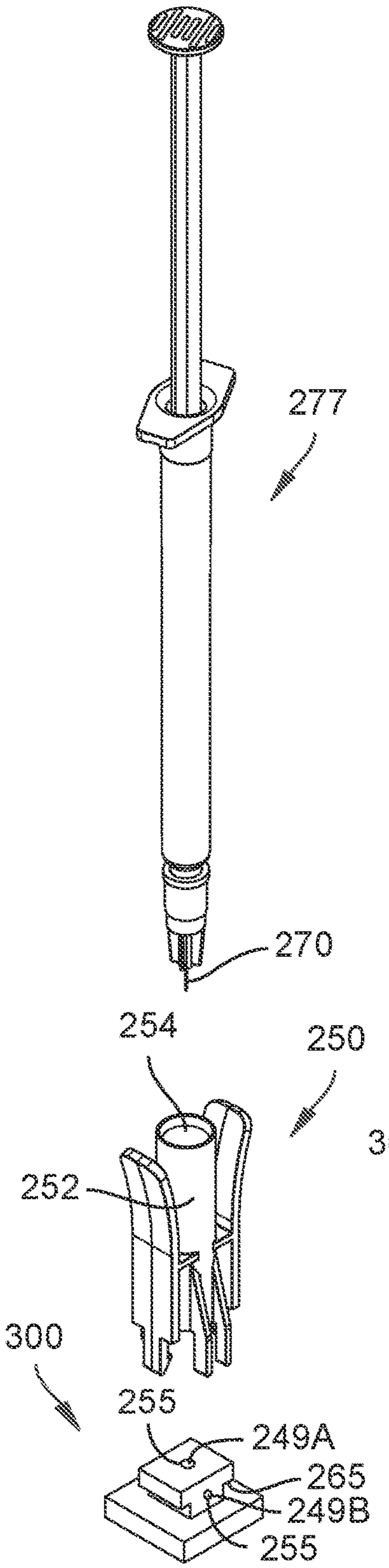
FIG. 18 depicts an exploded view of an example infusion set, example adapter, and example delivery implement.

An exemplary adapter 250 is depicted in FIGS. 18-20. An example adapter 250 may include an elongate body 252 with a bore 254 extending therethrough. A delivery implement 277 may be advanced into the bore 254 from one end of the adapter 250. The opposing end of the adapter 250 may include one or more coupler which may mate with a portion of the infusion set 300. Various coupler types may be used depending on the embodiment. The coupler(s) included in an adapter 250 may be dependent upon the type of infusion set 300 which the adapter 250 is intended for use with. Adapters 250 may twist, thread, snap, clip, bayonet mount, etc. to an infusion set 300 so long as the appropriate cooperating coupling features are provided on the infusion set 300. When an adapter 250 is attached to the infusion set 300, the delivery sharp 270 of a delivery implement 277 may be guided by the adapter 250 into the internal volume 302 (see, e.g., FIG. 17) through any intervening sealing member(s) 249 A, B. Where a tubing connector 263 includes a blunt delivery projection which may open any sealing member(s) 249A, B, the delivery implement 277 may include a similar blunt delivery member in place of a delivery sharp 270.

As shown in FIGS. 18-20, one exemplary adapter 250 which may be used with an infusion set 300 may include an elongate body 252 with a set of flanking arms 256. A bore 254 may also extend through the adapter 250. The first end 258 of each of the arms 256 may extend away (e.g. curve away) from the elongate body 252. The second end 262 of each of the arms 256 may include a catch 264 which serves as the coupler. In the example shown in FIGS. 18-20, the adapter 250 may interface with an infusion set 300 including a set of ledges 265 similarly to the ledges of the injection port 100 shown in FIG. 14. The catches 264 may each be associated a ramp which may aid in causing deflection of the arms 256 to the open state as the adapter 250 is pressed against the infusion set 300. An intermediate region 260 of the arms 256 may be connected to the elongate body 252. The end of the elongate body 252 proximal the second ends 262 of the arms 256 may include a number of standoffs 257. The standoffs 257 may be disposed against an exterior face or interface with externally accessible receiving area of the infusion set 300. The standoffs 257 may aid in firmly positioning the adapter 250 against the infusion set 300 and prevent displacement or wobbling of the adapter 250 when administering an injection via a delivery implement 277. Other embodiments of adapters 250 for use with injection ports 100 may include standoffs 257. Where an infusion set 300 includes a generally flat base with various features which are raised proud of the base, the standoffs 257 may be spaced so as to not interfere with any of the raised features. The example adapter 250 may be coupled and decoupled from the infusion set 300 as described in relation to FIGS. 13-14.

Figure 21:
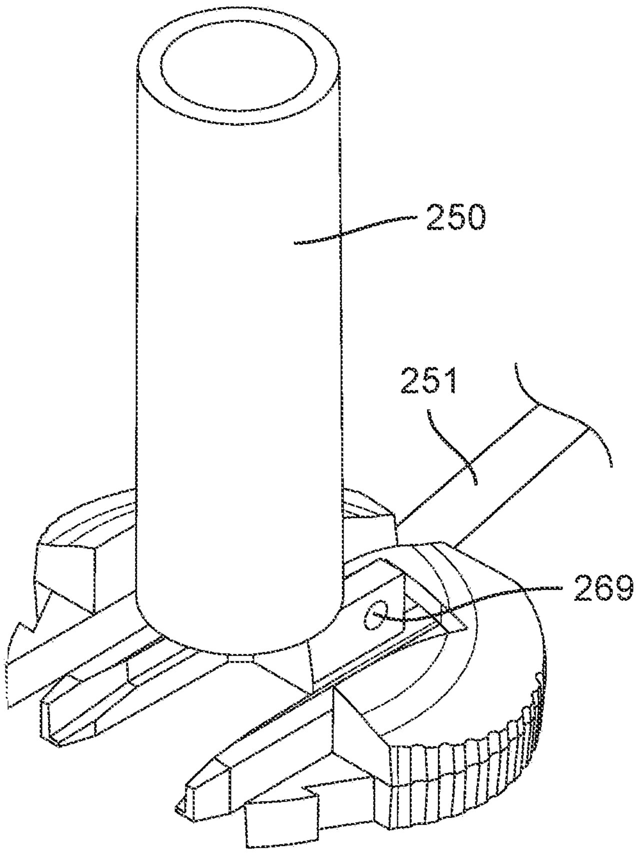
FIG. 21 depicts an example tubing connector with an example adapter.
Figure 22:
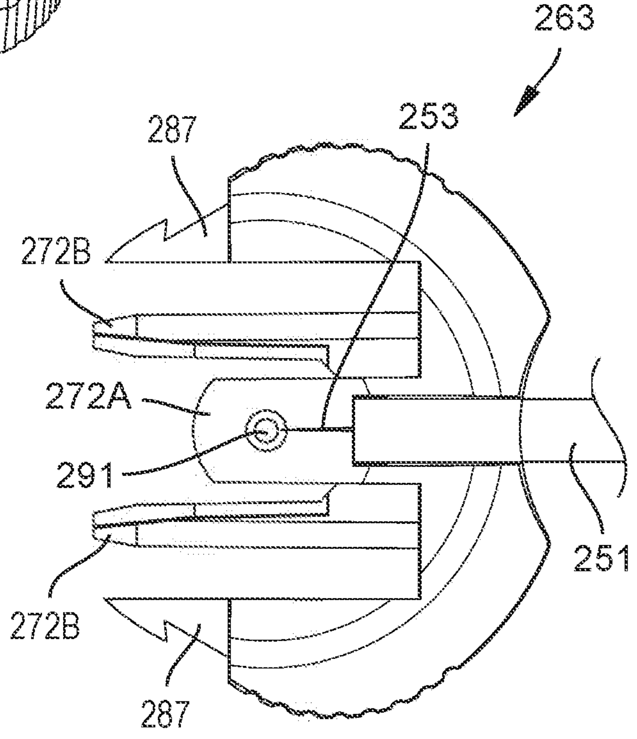
FIG. 22 depicts a bottom plan view of an example tubing connector.

Referring now to FIGS. 21-22, an exemplary tubing connector 263 is depicted. In some examples, a tubing connector 263 may accept or include an adapter 250. The adapter 250 may allow for a delivery implement 277 (see, e.g., FIG. 18) to deliver an injection into an infusion set 300 if desired. As shown, an adapter 250 may couple to a tubing connector 263. In some embodiments, the adapter 250 may be removable and attached to the tubing connector 263 via any suitable coupling arrangement (e.g. snap-fit into receptacles on the tubing connector 263). In alternative embodiments and as shown, the adapter 250 may be displaceable from a stowed state to an injection state. In the example embodiment, the adapter 250 is pivotally displaceable between the stowed state and injection state. The exemplary adapter 250 is coupled to the tubing connector 263 via a pivot pin 269.

In the stowed state, the exemplary adapter 250 may be lowered into a less obtrusive position close to or against the skin. In the injection state (shown), the adapter 250 may be disposed over an aperture 291 in a sharp flanking projection 272A of the tubing connector 263. Alternatively, where tubing connectors 263 do not include a sharp flanking projection 272A, the bore 254 of an adapter 250 may be aligned with an open space between coupling arms 287 or sharp flanking projections 272B of the tubing connector 263. The adapter 250 may be positioned in alignment with an access entry 255 (see, e.g., FIG. 20) to the interior volume 302 (see, e.g., FIG. 17) of the infusion set 300 when in the injection state. When the delivery sharp 270 (see, e.g., FIG. 18) of a delivery implement 277 (see, e.g., FIG. 18) is advanced into the adapter 250, the delivery sharp 270 may pass through the access entry 255 and into the internal volume 302 of the infusion set 300. Any sealing member(s) 249A, B (see, e.g., FIG. 17) between the internal volume 302 and the adapter 250 may be punctured (or opened if, for instance, a split septum is present) by the delivery sharp 270 (or blunt delivery member where a split septum is used) of the delivery implement 277. The adapter 250 may act as a guide which facilitates alignment with the access entry 255 to the internal volume 302.

The delivery sharp 270 of the delivery implement 277 may be selected so as to have a length which ensures the delivery sharp 270 cannot contact a delivery projection 253 of the tubing connector 263. Alternatively or additionally, the adapter 250 may include a stop (e.g. step or ledge) which prevents the delivery implement 277 from being advanced beyond a certain distance. This may inhibit the delivery sharp 270 from contacting the delivery projection 253 of the tubing connector 263. Where the tubing connector 263 is removed prior to use of an adapter 250, the stop may prevent the delivery sharp from contacting the dispensing body 304 (see, e.g. FIG. 17).

Though shown attached to a tubing set connector 263 with infusion tubing 251 and a connector sharp 253, a dedicated connector 282 (see, e.g., FIG. 23) with an attached (or attachable/detachable) adapter 250 may be used in certain examples. Such a dedicated connector 282 may not include a delivery projection 253 or be attached to infusion tubing 251. Fluid passages through the dedicated connector 282 may also be omitted. The dedicated connector 282 may otherwise look the same as a tubing connector 263 intended for use with a particular infusion set 300. Such a dedicated connector 282 for an example infusion set 300 is shown in FIG. 23.

Figure 23:
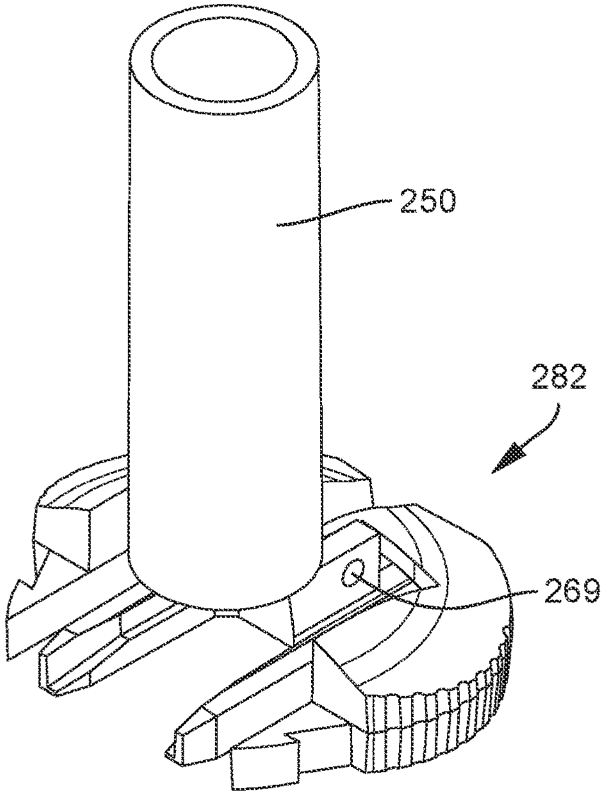
FIG. 23 depicts a view of an example dedicated connector which includes an example adapter.

Referring primarily to FIG. 23, in some examples, an adapter 250 may be static and disposed in the injection position or even formed integrally with such a dedicated connector 282. When a manual injection via an infusion set 300 is desired, a tubing connector 263 (see, e.g., FIG. 20) may be decoupled from the infusion set 300 and the dedicated connector 282 bearing the adapter 250 may be coupled in place in its stead. A delivery implement 277 (see, e.g., FIG. 18) may be advanced into the adapter 250 to perform the injection and the dedicated connector 282 may be subsequently removed and replaced by the tubing connector 263. Therapy via delivery of agent from an infusion pump 293 (see, e.g., FIG. 20) through the tubing connector 263 may then be resumed.

Figure 24:
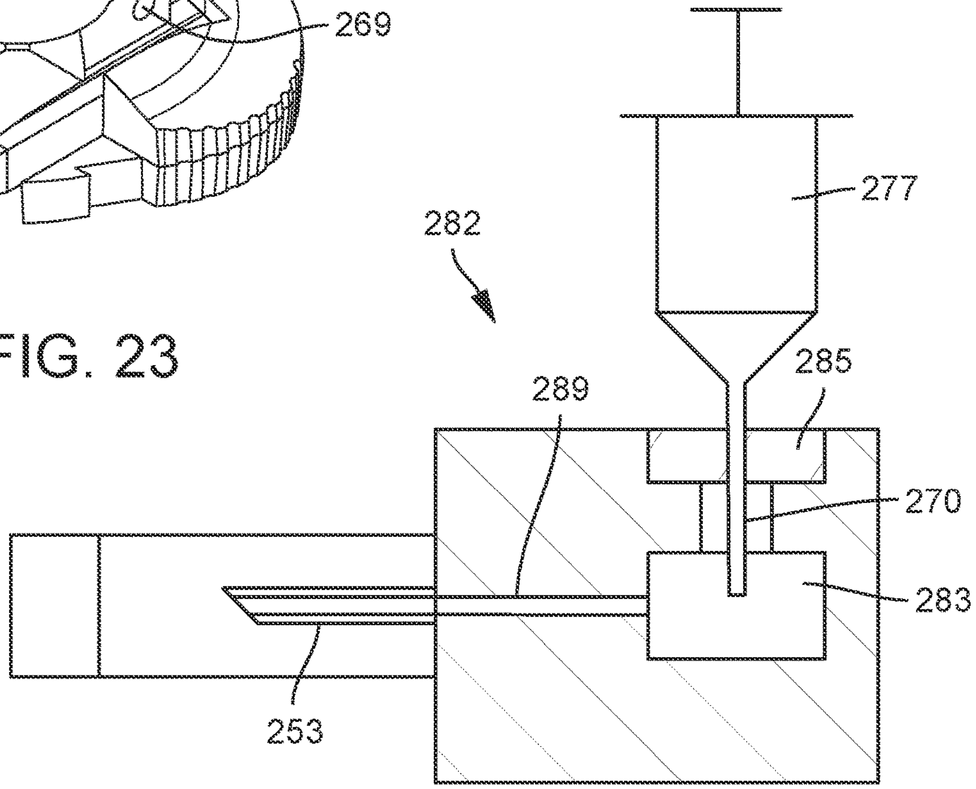
FIG. 24 depicts a view of an example dedicated connector which includes an injection port which may be used to deliver an agent into the dedicated connector.

In still other embodiments and referring now to FIG. 24, a dedicated connector 282 may provide access to an internal volume of an infusion set 300 without use of an adapter 250. For example, the dedicated connector 282 may look generally the same as any tubing set connector 263 (see, e.g., FIG. 20) intended for use with the infusion set 300. The dedicated connector 282 may not be attached to any tubing 251. The dedicated connector 282 may include a delivery projection 253 which may be in fluid communication via a fluid flow path 289 with an injection receiving volume 283 defined within the dedicated connector 282. The injection receiving volume 283 may be accessible from the exterior of the dedicated connector 282 via a sealing member (e.g. membrane or septum) 285. With such a dedicated connector 282 attached to the infusion set 300, a delivery sharp 270 of a delivery implement 277 may be advanced through the sealing member 285 and into communication with the injection receiving volume 283. In some embodiments, an adapter 250 may be attached to or provided as part of a dedicated connector 282 (see, e.g., FIG. 21) to aid in aligning a delivery sharp 270 with the sealing member 285. Fluid from the delivery implement 277 may be dispensed into the dedicated connector 282 and may pass through the connector sharp 253 and into the patient via the infusion set 300. The dedicated connector 282 may be subsequently removed and replaced by the tubing connector 263. Therapy via delivery of agent from an infusion pump 293 (see, e.g., FIG. 20) through the tubing connector 263 may then be resumed.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. An injection port assembly for delivery of multiple injections to a patient comprising:

a support body comprising:

a main body with a sole passage extending through the main body;

a receptacle including a receptacle wall extending from a first face of the main body and surrounding the sole passage, the receptacle wall including at least one recess extending across a face of the receptacle wall most distal to the main body and a plurality of cantilevered retainer members;

a plurality of sections proud of the first face, the plurality of sections including a peripheral rim at the periphery of the main body and a number of proud sections extending from the receptacle wall to the peripheral rim, the number of proud sections each having a height dimension which is substantially even with a height dimension of the peripheral rim where each of the number of sections meets the peripheral rim; and an adhering body attached to a second face of the main body opposite the first face; and a delivery assembly retained within the receptacle by the retainer members, the delivery assembly having a cannula with an enlarged end region, the cannula extending through the sole passage, the delivery assembly including a barrier defining a cavity within which the enlarged end region is at least partially contained, a face of the enlarged end region most distal an outlet of the cannula being against a flat face of the cavity, a sole externally accessible portion of the barrier being aligned with an axis of the cannula.

2. The injection port assembly of claim 1, wherein at least a portion of the receptacle wall most distal to the first face includes a taper.

3. The injection port assembly of claim 1, wherein each of the at least one recess includes a taper at least at a portion of each of the at least one recess which is most distal to the first face.

4. The injection port assembly of claim 1, wherein each of the retainer members include a ramped latching protuberance at an unsupported end of each of the retainer members.

5. The injection port assembly of claim 1, wherein the delivery assembly includes a set of notches each configured to engage with a respective retainer member of the plurality of retainer members.

6. The injection port assembly of claim 1, wherein the delivery assembly includes a number of ear projections equal to the number of the at least one recess in the receptacle wall, each ear projection being disposed in one of the at least one recess in the receptacle wall.

7. The injection port assembly of claim 1, wherein the barrier is constructed of a self-sealing material which self-seals after removal of a deliver sharp that has pierced the barrier.

8. The injection port assembly of claim 1, wherein the injection port assembly further comprises a medicament injecting implement adapter, the medicament injecting implement adapter configured to couple to the support body.

9. The injection port assembly of claim 8, wherein the medicament injecting implement adapter includes an adapter receptacle for accepting a medicament injecting implement, the medicament injecting implement adapter receptacle disposed over the sole externally accessible portion of the barrier when coupled to the support body.

10. The injection port assembly of claim 8, wherein the receptacle wall includes a number of ledges and the medicament injecting implement adapter includes a number of latching arms, each latch arm configured to engage with a respective ledge of the number of ledges.

11. The injection port assembly of claim 8, wherein the sole exposed portion of the barrier is spaced from the injection receiving volume by a barrier distance and the medicament injecting implement adapter includes a stop which limits a delivery sharp of a medicament injecting implement from advancing into the injection port assembly to a depth greater than the barrier distance plus a percentage of a height of the injection receiving volume, the percentage being less than 100%.

12. The injection port of claim 1, wherein, an outwardly facing sealing surface of the enlarged end region forms a fluid tight seal against the barrier.

13. An injection port assembly for delivery of multiple injections to a patient comprising:

a support body having a sole passage extending through the support body;

a receptacle including a receptacle wall surrounding the sole passage, the receptacle wall including at least one recess across an end surface of the receptacle wall recessed toward the support body, the receptacle wall including a plurality of cantilevered retainer members;

a plurality of ribs including a guard rim rib at the periphery of the support body and a number of additional ribs extending from the receptacle wall to the guard rim rib, an end of the guard rim rib most distal the support body being substantially even with an end of each of the additional ribs most distal the support body where each of the additional ribs meet the guard rim rib;

an adhering body attached to the support body; and a delivery assembly coupled within the receptacle via engagement with the retainer members, the delivery assembly having a cannula with an enlarged end region, the cannula extending through the sole passage, the delivery assembly having a barrier with a sole externally accessible portion aligned with an axis of the cannula, a face of the enlarged end region most distal an outlet of the cannula being against a flat face of a cavity defined in the barrier within which the enlarged end region is at least partially disposed.

14. The injection port assembly of claim 13, wherein the receptacle wall includes a tapered portion.

15. The injection port assembly of claim 13, wherein each of the at least one recess includes a tapered portion.

16. The injection port assembly of claim 13, wherein each of the retainer members include a ramped latching protuberance at an unsupported end of each of the retainer members.

17. The injection port assembly of claim 13, wherein the delivery assembly includes a set of retention recesses each configured to engage with a respective retainer member of the plurality of retainer members.

18. The injection port assembly of claim 13, wherein the delivery assembly includes a number of ear projections equal to the number of the at least one recess in the receptacle wall, each ear projection being disposed in one of the at least one recess in the receptacle wall when the delivery assembly is coupled within the receptacle.

19. The injection port assembly of claim 13, wherein the barrier is constructed of a self-sealing elastomer.

20. The injection port assembly of claim 13, wherein the injection port assembly further comprises a medicament injecting implement adapter configured to couple to the receptacle wall.

21. The injection port assembly of claim 20, wherein the medicament injecting implement adapter includes an adapter receptacle for accepting a medicament injecting implement, the medicament injecting implement adapter receptacle disposed over the sole externally accessible portion of the barrier when coupled to the support body.

22. The injection port assembly of claim 20, wherein the receptacle wall includes a number of ledges and the medicament injecting implement adapter includes a number of latching arms, each latch arm configured to engage with a respective ledge of the number of ledges.

23. The injection port assembly of claim 20, wherein the sole exposed portion of the barrier is spaced from the injection receiving volume by a barrier distance and the medicament injecting implement adapter includes a stop which limits a delivery sharp of a medicament injecting implement from advancing into the injection port assembly to a depth greater than the barrier distance plus a percentage of a height of the injection receiving volume, the percentage being less than 100%.

24. The injection port assembly of claim 13, wherein the enlarged end region has an outwardly facing sealing surface which forms a fluid tight seal against the barrier.

25. An injection port assembly for delivery of multiple injections to a patient comprising:

a support body having a sole passage therethough and a receptacle associated with the sole passage, the receptacle having at least one notched recess across an end surface of the receptacle opposite the support body, the receptacle having a plurality of cantilevered retainer members;

a plurality of ribs including a guard rim rib about at periphery of the support body and a number of additional ribs extending from the receptacle to the guard rim rib, a height of each of the number of additional ribs decreasing to a height of the guard rim rib as distance to the periphery of the support body decreases; and a delivery assembly latched within the receptacle via the retainer members, the delivery assembly having a cannula extending through the sole passage, the cannula including an end region defining an end region interior volume within the end region in fluid communication with a lumen of the cannula and otherwise sealed from the surrounding environment by a self-sealing barrier, a sole externally accessible portion of the barrier being aligned with an axis of the lumen, the delivery assembly devoid of open volumes in communication with the cannula other than the end region interior volume.

* * * * *